United States Patent
Shultz et al.

(10) Patent No.: US 6,379,898 B2
(45) Date of Patent: Apr. 30, 2002

(54) NUCLEIC ACID DETECTION

(76) Inventors: John W. Shultz, 467 Melody La., Verona, WI (US) 53593; Michelle A. Nelson, 2945 Fish Hatchery Rd., #2, Fitchburg, WI (US) 53713; Donna M. Leippe, 4833 Sheboygan Ave. #328, Madison, WI (US) 53705; Martin K. Lewis, 5210 Forge Dr., Madison, WI (US) 53716; Lisa S. Nelson, 7881 Helmke Rd., DeForest, WI (US) 53532

( * ) Notice: Subject to any disclaimer, the term of this patent is extended or adjusted under 35 U.S.C. 154(b) by 0 days.

(21) Appl. No.: 09/757,132

(22) Filed: Jan. 9, 2001

Related U.S. Application Data

(63) Continuation of application No. 09/042,287, filed on Mar. 13, 1998, now Pat. No. 6,335,162.

(51) Int. Cl.[7] ............................. C12Q 1/68; G01N 33/53
(52) U.S. Cl. .................................... 435/6; 435/7.1
(58) Field of Search ............................. 435/6, 7.1, 91.2

(56) References Cited

U.S. PATENT DOCUMENTS

| | | | |
|---|---|---|---|
| 4,303,752 A | 12/1981 | Kolemainen et al. | 435/8 |
| 4,331,762 A | 5/1982 | Nakajima et al. | 435/190 |
| 4,338,395 A | 7/1982 | Leon et al. | 435/17 |
| 4,352,881 A | 10/1982 | Inagawa et al. | 435/17 |
| 4,357,420 A | 11/1982 | Bostick et al. | 435/8 |
| 4,368,261 A | 1/1983 | Klose et al. | 435/15 |
| 4,371,611 A | 2/1983 | Fusee | 435/14 |
| 4,394,445 A | 7/1983 | Nix et al. | 435/19 |
| 4,415,655 A | 11/1983 | de Castro et al. | 435/17 |
| 4,438,124 A | 3/1984 | Meister et al. | 424/270 |
| 4,443,594 A | 4/1984 | Buckmann | 536/27 |
| 4,446,231 A | 5/1984 | Self | 435/7 |
| 4,460,684 A | 7/1984 | Bauer | 435/14 |
| 4,485,177 A | 11/1984 | Siedel et al. | 436/547 |
| 4,595,655 A | 6/1986 | Self | 435/7 |
| 4,735,897 A | 4/1988 | Vary et al. | 435/17 |
| 4,743,561 A | 5/1988 | Shaffar | 436/501 |
| 4,755,158 A | 7/1988 | Rabbani et al. | 435/5 |
| 5,356,776 A | 10/1994 | Kambara et al. | 435/6 |
| 5,391,480 A | 2/1995 | Davis et al. | 435/6 |
| 5,403,711 A | 4/1995 | Walder et al. | 435/6 |
| 5,494,810 A | 2/1996 | Barany et al. | 435/91.52 |
| 5,498,523 A | 3/1996 | Tabor et al. | 435/6 |
| 5,530,192 A | 6/1996 | Murase et al. | 800/205 |
| 5,622,824 A | 4/1997 | Koster et al. | 435/6 |
| 5,648,232 A | 7/1997 | Squirrell | 435/34 |
| 5,660,988 A | 8/1997 | Duck et al. | 435/6 |
| 5,683,877 A | 11/1997 | Lu-Chang et al. | 435/6 |
| 5,731,146 A | 3/1998 | Duck et al. | 435/6 |
| 5,741,635 A | 4/1998 | Boss et al. | 435/4 |
| 5,763,181 A | 6/1998 | Han et al. | 435/6 |
| 5,786,139 A | 7/1998 | Burke et al. | 435/6 |
| 5,871,902 A | 2/1999 | Weininger et al. | 435/6 |
| 5,902,722 A | 5/1999 | Di Cesare et al. | 435/4 |
| 6,007,987 A | 12/1999 | Cantor et al. | 435/6 |
| 6,066,483 A | 5/2000 | Riggs et al. | 435/194 |

FOREIGN PATENT DOCUMENTS

| | | | |
|---|---|---|---|
| EP | 0 229 601 A | 11/1986 | |
| EP | 639 647 A | 7/1994 | |
| EP | 0 663 447 A | 12/1994 | |
| EP | 0 894 867 A | 11/1997 | |
| GB | 2055200 | 12/1981 | ......... G01N/21/76 |
| GB | PCTWO94/25619 | 11/1994 | ............ C12Q/1/00 |
| WO | WO 90/05530 | 5/1990 | |
| WO | WO 91/17264 | 11/1991 | |
| WO | WO 92/13963 | 8/1992 | |
| WO | WO 94/25619 | 11/1994 | |
| WO | WO 95/21938 | 8/1995 | |
| WO | WO 96/41014 | 12/1996 | |
| WO | WO 97/41256 | 11/1997 | |
| WO | WO 98/13523 | 4/1998 | |
| WO | WO 98/54362 | 4/1998 | |
| WO | WO 98/28440 | 7/1998 | |

OTHER PUBLICATIONS

Sippel, A.E., Purification and Characterization of Adenosine Triphosphate: Ribonucleic Acid Adenyltransferase from *Escherichia coli, Eur. J. Biochem.* 37, 31–40 (1973) –published sufficiently before filing date such that the month is not an issue.

Chowdhury, K.,N. Kaushik, V.N. Pandey, and M.J. Modak, "Elucidation of the Role of Arg 110 of Murine Leukemia Virus Reverse Transcriptase in the Catalytic Mechanism: Biochemical Characterization of Its Mutant Enzymes", *Bichem.* 35: 16610–20 (1996) –published sufficiently before filing date such that the month is not an issue.

Karamohamed, S., M. Ronaghi, and P. Nyren, "Biolumino-metric Method for Real–Time Detection of Reverse Transcriptase Activity", *BioTechniques* 24:302–306 (Feb. 1998).

(List continued on next page.)

*Primary Examiner*—Eggerton A. Campbell
(74) *Attorney, Agent, or Firm*—Welsh & Katz, Ltd.

(57) ABSTRACT

This invention discloses methods, compositions and kits for the detection of extremely low levels of nucleic acid, cells and cellular material in biological samples. The nucleic acid detection systems utilize either the pyrophosphorolysis reaction catalyzed by various polymerases or nuclease digestion coupled with pyrophosphorylation catalyzed by phosphoribosylpyrophosphate synthetase to produce either deoxyribonucleoside triphosphates or ribonucleoside triphosphates. dNTPs are transformed to ATP by the action of nucleoside diphosphate kinase. The ATP produced by these reactions may be detected by luciferase or NADH based detection systems. If more sensitive detection is required, schemes for the amplification of NTPs and dNTPS are provided. A detection system for cells or cellular material in a sample is provided wherein AMP and a high energy phosphate donor added to a sample are converted to ATP by the action of endogenous enzymes, followed by detection of the ATP.

8 Claims, No Drawings

OTHER PUBLICATIONS

Hove–Jensen, B., K. W. Harlow, C. J. King, R. L. Switzer, "Phosphoribosylpyrophosphate Synthetase of *Escherichia coli*", *J. Biol. Chem.* 261 (15) 6765–71 (1986) –published sufficently before filing date such that the month is not an issue.

Nyren, P., S.Karamohamed, and M. Ronaghi, "Detection of Single–Base Changes Using a Bioluminometric Primer Extension Assay", *Anal. Biochem.*, 344: 267–73 (Jan. 15, 1997).

Ronaghi, M., S. Karamohamed, B. Pettersson, M. Uhlen, P. Nyren, "Real–Time DNA Sequencing Using Detection of Pyrophosphate Release", *Anal. Biochem.*, 242: 84–89 (1996) –published sufficiently before filing date such that the month is not an issue.

Rozovskaya, T. A., V.O. Rechinsky, R. S. Bibilashvili, M. Y. Karpeisky, N. B. Tarusova, R. M. Khomutov, H. B. F. Dixon, "The Mechanism of Pyrophosphorolysis of RNA by RNA Polymerase", *Biochem J.*, 224: 645–650 (1989) –published sufficiently before filing date such that the month is not an issue.

Deutscher, M. P., and A. Kornberg, "Enzymatic Synthesis of Deoxyribonucleic Acid", *J. Biol. Chem.* 224 (11): 3019–28 (1969) –published sufficiently before filing date such that the month is not an issue.

Moyer, J. D., and J. F. Henderson, "Nucleoside Triphosphate Specificity of Firefly Luciferase", *Anal. Biochem.* 131: 187–189 (1983) –published sufficiently before filing date such that the month is not an issue.

Blondin, C., L. Serina, L. Wiesmuller, A. Gilles, and O. Barzu, "Improved Spectrophotometric Assay of Nucleoside Monophosphate Kinase Activity Using the Pyruvate Kinase/Lactate Dehydrogenase Coupling System", *Anal. Biochem.* 220: 219–21 (1994) –published sufficiently before filing date such that the month is not an issue.

Tabor, S., and C. C. Richardson, "DNA Sequence Analysis With a Modified Bacteriophage T7 DNA Polymerase", *J. Biol. Chem.*, 265 (14) 8332–28 (1990) –published sufficiently before filing date such that the month is not an issue.

Chittock, R. S., J–M. Hawronsky; J. Holah, and C. W. Wharton, "Kinetic Aspects of ATP Amplification Reactions", *Anal. Biochem.* 255: 120–26 (Jan. 1, 1998).

Kung, et al., "Picogram Quantitation of Total DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Based Changes Using a Bioluminometric Primer Extension Assay", *Annal. Biochem.*, 244:367–373 (1997).

P. Bernard et al., *Am. J. Pathol.*, 153:1055–1061 (1998).

G. Garinis et al., *J. Clin. Lab. Anal.*, 13: 122–125 (1999).

Holguin, et al., *Eur. J. Clin. Microbiol. Infect. Dis.*, 18:256–259 (1990).

Boriskin, et al., *Arch. Dis. Child.*, 80:132–136 (1999).

de Vega, et al., "Primer Terminus Stabilizing at the 3'–5' exonuclease active site of 29 DNA polymerase. Involvement of two amino acid residues highly conserved in proffreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison,http://www.bact.wisc.edu/bact102/102dil3.html.

J. Lindquist, Dept. of Bacteriology, University of Wisconsin–Madison, http://www.bact.wisc.edu/bact102/102dil3a.html.

Most Probable Number (MPN), WQA Glossary of Terms, 3rd Ed., Water Quality Association.

P. Nyren, B. Petterson, and M. Uhlen. "Solid Phase DNA Minisequencing byan Enzymatic Luminometric Inorganic Pyrophosphate Detection Assay, ". *Anal. Biochem..*, 208:171–175 (1993).

M. Ronaghi, S. Karamohamed, B. Petterson, M. Uhlen, and P. Nyren, "Real–Time DNA Sequencing Using Detection of Pyrophosphate Release," *Anal. Biochem.*, 242:84–89 (1996).

Seq ID No.1, "Blast Archaeal Gemone Sequences at Center of marine Biotechnology" Online, May 21, 1999, Retrieved on Aug. 7, 200 @ http://combdna. umbi.umd.edu/bags.html. HTTP:/Comb5–156.Umbi.Umd.Edu/cgi–Bin–PfurGene-.PL?GeneID=894645&Dataset=Nayb&Geneidtxt–894645, Online649 XP002144446, Retrieved from the internet on Aug. 7, 2000.

Giartosio, et al., "Thermal stability of hexameric and tetrameric nucleoside diphosphatekinases: Effect of subunit interaction.", J. Biol. Chem, 271:30:17845–17851 (1996).

Bi, W., et al., "Detection of known mutation by proof–reading PCR", Nucleic Acid Research, GB, 26:12:3073–3075 (1998).

Kawarabayashi, et al., Complete Sequence and Gene Organization of the Genome of Hyper–thermophilic Archaebacterium, *Pyrococcus horikoshii* OT3, DNA Research, 5:55–76 (1998).

NUCLEIC ACID DETECTION

CROSS-REFERENCE TO RELATED APPLICATIONS

This application is a continuation of U.S. Ser. No. 09/042,287, filed Mar. 13, 1998 U.S. Pat. No. 6,335,162.

FIELD OF THE INVENTION

The present invention relates to the field of molecular biology, and in particular to the detection of nucleic acids and cells. Methods and compositions for detection of extremely low amounts of nucleic acids and cellular materials with ATP based detection systems are described.

BACKGROUND

Methods for producing large amounts of recombinant protein are well known. As the recombinant protein industry has developed, the need for various quality control assays has arisen. An example is the need for the quantitation of nucleic acids present in recombinant protein preparations. Current guidelines require that the amount of nucleic acid present in recombinant therapeutic proteins be less than 10 pg of DNA per daily dose of recombinant protein. Therefore, methods for detecting extremely low amounts of nucleic acids are needed. Such methods would also find widespread use for the quantitation of DNA in forensic samples.

Several methods of detecting low levels of nucleic acid have been described. The first method is based on classical hybridization techniques. This method utilizes radio-labeled nucleic acid probes which bind to the DNA of interest. However, this method has several disadvantages including poor reproducibility, generation of large amounts of waste reagent, and high background levels caused by nonspecific binding. Furthermore, this technique is generally inappropriate for determining the presence of low amounts of DNA of unknown sequence.

A second method of detecting nucleic acid utilizes fluorescent dyes capable of intercalating into nucleic acids. However, many interfering substances such as detergents, proteins, and lipids affect the reproducibility of the signal generated by this method.

A third method of detecting low levels of DNA utilizes biotinylated single-stranded DNA binding protein (SSB), streptavidin, an anti-DNA antibody fused to urease, and biotinylated nitrocellulose as reagents. This assay is commercially available from Molecular Devices and described in Kung et al., Picogram Quantitation of Total DNA Using SNA-Binding Proteins in a Silicon Sensor-Based System, Anal. Biochem. 187: 220–27 (1990). The assay is performed by incubating the streptavidin, biotin-SSB, and the anti-DNA antibody together, allowing a complex to be formed. The complex is then captured on the biotinylated filter, washed, and the amount of captured urease is read. This method is highly sensitive but has several disadvantages. These disadvantages include costly reagents and the need for extensive controls.

A fourth method involves the depolymerization or degradation of nucleic acids and detection of ATP by luciferase. Polynucleotide polymerases are responsible for the synthesis of nucleic acids in cells. These enzymes are also capable of catalyzing other reactions as described in Deutscher and Kornberg, Enzymatic Synthesis of Deoxyribonucleic Acid, J. Biol. Chem. 244(11):3019–28 (1969). Many, but not all, polymerases are able to depolymerize nucleic acid in the presence of either phosphate or pyrophosphate.

U.S. Pat. No. 4,735,897 describes a method of detecting polyadenylated messenger RNA (poly(A)-mRNA). Depolymerization of poly(A)-mRNA in the presence of phosphate has been shown to result in the formation of ADP, which can be converted by pyruvate kinase or creatine phosphokinase into ATP. RNA may also be digested by a ribonuclease to AMP, converted to ADP by adenylate kinase, and then converted to ATP by pyruvate kinase.

The ATP so produced is detected by a luciferase detection system. In the presence of ATP and O2, luciferase catalyzes the oxidation of luciferin, producing light which can then be quantitated using a luminometer. Additional products of the reaction are AMP, pyrophosphate and oxyluciferin.

The presence of ATP-generating enzymes in all organisms also allows the use of a luciferase system for detecting the presence or amounts of contaminating cells in a sample, as described in U.S. Pat. No. 5,648,232. For example, ADP may be added to a sample suspected of containing contaminating cells. The ADP is converted by enzymes of the cell into ATP which is detected by a luciferase assay, as described above. The disadvantage of this method is the relative instability of the ADP substrate.

What is needed in the art are reliable, cost-effective methods of detecting extremely low levels of nucleic acids, cells, and cellular material in a wide variety of samples. The present invention discloses novel methods for detecting low quantities of DNA, RNA and of cells. These methods take advantage of novel combinations of pyrophosphorolysis or enzymatic degradation of nucleic acids, conversion of dNTPs to ATP, the conversion of AMP directly to ATP, amplification of ATP to increase sensitivity, depolymerization of oligonucleotide probes, and optimized reaction conditions.

SUMMARY OF THE INVENTION

A need exists for quality control assays for proteins produced by recombinant methods. Current guidelines suggest that preparations of recombinant protein should contain less than 10 picograms of nucleic acid. There is also a need to be able to quantitate extremely low levels of nucleic acids in forensics samples. Therefore, it is an object of the present invention to provide methods for detecting low amounts of nucleic acids and low numbers of cells or cellular material. It is also an object of the invention to provide compositions for the detection of nucleic acids and kits for the detection of nucleic acids.

In one embodiment of the present invention a method is provided for detecting and/or assaying deoxyribonucleic acid in a reaction containing phosphate, adenosine 5'-diphosphate, or a combination thereof. The method comprises depolymerizing the nucleic acid at a terminal nucleotide by enzymatically cleaving the terminal internucleoside phosphodiester bond and reforming same with a pyrophosphate molecule to form a deoxyribonucleoside triphosphate molecule according to the following reaction:

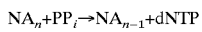

$NA_n + PP_i \rightarrow NA_{n-1} + dNTP$ catalyzed by a DNA polymerase or reverse transcriptase selected from the group consisting of T4 polymerase, Taq polymerase, AMV reverse transcriptase, and MMLV reverse transcriptase. In a quantitative assay for nucleic acids, the depolymerizing step is repeated essentially to completion or equilibrium to obtain at least two nucleoside triphosphate molecules from a strand of minimally three nucleotides. For detection of DNA, the depolymerizing step need not be repeated if there are sufficient nucleic acid molecules present to generate a signal. The next step involves enzymatically transferring terminal 5' phosphate groups from the deoxyribonucleoside triphosphate molecules to an adenosine 5'-diphosphate molecule to form adenosine 5'-triphosphate according to the following reaction:

$$dNTP^*+ADP \rightarrow NDP+ATP^*$$

catalyzed by nucleoside diphosphate kinase and wherein P* is the terminal 5' phosphate so transferred. The final step is the detection of the ATP, either by a luciferase detection system or NADH detection system. The depolymerizing step and phosphate transferring step may optionally be performed in a single pot reaction. If greater sensitivity is desired, the ATP molecules produced by the phosphate transferring step or the NTPs produced by the depolymerizing step may be amplified to form a plurality of ATP molecules.

In another embodiment of the present invention, a method is provided for detecting polyadenylated mRNA in a reaction containing pyrophosphate. The polyadenylated mRNA is first depolymerized at a terminal nucleotide by enzymatically cleaving the terminal internucleoside phosphodiester bond and reforming same with a pyrophosphate molecule to form a free ATP molecule according to the following reaction:

$$NA_n+PP_i \rightarrow NA_{n-1}+ATP$$

catalyzed by poly(A) polymerase. In a quantitative assay for RNA, the depolymerizing step is repeated essentially to completion or equilibrium to obtain at least two nucleoside triphosphate molecules from a strand of minimally three nucleotides. For detection of DNA, the depolymerizing step need not be repeated if there are sufficient nucleic acid molecules present to generate a signal. The ATP molecules so formed are then detected with either a luciferase detection system or a NADH detection system. The sensitivity of the reaction may be increased by optionally amplifying the ATP molecules.

In another embodiment of the present invention, a method is provided for selectively detecting and/or assaying poly(A) mRNA in a reaction containing pyrophosphate, adenosine 5'-diphosphate, or a combination thereof. In this method, a complementary oligo (dT) probe is hybridized to poly(A) mRNA to form an RNA-DNA hybrid. The oligo (dT) strand of the RNA-DNA hybrid is then depolymerized at the terminal nucleotide by enzymatically cleaving the terminal internucleotide phosphodiester bond and reforming same with a pyrophosphate molecule to form deoxythymidine 5'-triphosphate. According to the following reaction:

$$TT_n+PP_i \rightarrow TT_{n-1}+dTTP$$

catalyzed by a reverse transcriptase. In a quantitative assay for nucleic acids, the depolymerizing step is repeated essentially to completion or equilibrium to obtain at least two nucleotide triphosphate molecules from a strand of minimally three nucleotides. For detection of DNA, the depolymerizing step need not be repeated if there are sufficient nucleic acid molecules present to generate a signal. Next, the phosphate groups from the deoxythymidine 5'-triphosphate are enzymatically transferred to adenosine 5'-diphosphate molecules to form ATP molecules according to the following reaction:

$$dTTP^*+ADP \rightarrow dTDP+ATP^*$$

catalyzed by NDPK, wherein P* is the terminal 5' phosphate so transferred. Finally, the ATP so formed is detected by a luciferase detection system or an NADH detection system. If increased sensitivity is desired, the terminal phosphate of the dTTP may be transferred to ADP to form ATP as above followed by an amplification of the resulting ATP.

In another embodiment of the present invention, a method is provided of detecting DNA in a reaction containing phosphoribosylpyrophosphate, adenosine 5'-diphosphate, or a combination thereof. In this method, free deoxyribonucleoside monophosphate molecules are produced from the nucleic acid by digestion with a nuclease. A pyrophosphate group is then enzymatically transferred from phosphoribosylpyrophosphate molecules to the deoxyadenosine monophosphate molecules to form deoxyadenosine triphosphate molecules according to the following reaction:

$$dAMP+PRPP \rightarrow dATP+ribose\text{-}5\text{-}PO_4$$

catalyzed by phosphoribosylpyrophosphate synthetase. Next, the terminal 5' phosphate groups from the deoxyadenosine triphosphate molecules are enzymatically transferred to adenosine 5'-diphosphate molecules to form ATP molecules according to the following reaction:

$$dATP^*+ADP \rightarrow dADP+ATP^*$$

catalyzed by NDPK wherein P* is a terminal 5' phosphate so transferred. The ATP so produced may be detected by a luciferase detection system or an NADH detection system. If desired, the pyrophosphate transferring step and the phosphate transferring step may be performed in a single pot reaction. If increased sensitivity is required, the ATP molecules may be amplified.

Another embodiment of the present invention provides a method of detecting RNA in a reaction containing phosphoribosylpyrophosphate. Free ribonucleoside monophosphate molecules are produced by digestion of RNA with a nuclease. Next, a pyrophosphate molecule from phosphoribosylpyrophosphate molecules is enzymatically transferred to the adenosine monophosphate molecules to form adenosine triphosphate molecules according to the following reaction:

$$NMP+PRPP \rightarrow NTP+ribose\text{-}5\text{-}PO_4$$

catalyzed by phosphoribosylpyrophosphate synthetase. The ATP so produced is then detected by a luciferase detection system or an NADH detection system. If increased sensitivity is required, the ATP so produced may be amplified.

Another embodiment of the present invention provides a method for determining the presence and/or amount of cells and cellular material present in the sample. In this method, the contents of cells are released to form a cell lysate. Phosphate donor molecules and adenosine 5'-monophosphate molecules are then added to the cell lysate so that adenosine 5'-diphosphate molecules are produced by the enzymatic transfer of an phosphate group from the donor to the adenosine 5'-monophosphate according to the following reaction:

$$D\text{-}P+AMP \rightarrow D+ADP$$

catalyzed by endogenous enzymes present in the cell lysate. ATP is then produced by the enzymatic transfer of a phosphate from the donor molecules to adenosine 5'-diphosphate molecules according to the following reaction:

$$D\text{-}P+ADP \rightarrow D+ATP$$

also catalyzed by endogenous enzymes present in the cell lysate sample. The adenosine 5'-triphosphate so produced is then detected by either a luciferase detection system or an NADH detection system. The phosphate donor of this embodiment may be either deoxycytidine 5'-triphosphate, deoxyguanidine 5'-triphosphate, or deoxythymidine 5'-triphosphate.

The present invention further provides a composition of matter for producing adenosine 5'-triphosphate from DNA, pyrophosphate, and adenosine 5'-diphosphate. This composition comprises a mixture of nucleoside diphosphate kinase and a nucleic acid polymerase which are provided in a concentration sufficient to catalyze the production of ATP from DNA at about picogram to microgram amounts of DNA.

The present invention, also provides a composition of matter for producing adenosine triphosphate from DNA, phosphoribosylpyrophosphate, and adenosine 5'-diphosphate. This composition comprises a mixture of a phosphoribosylpyrophosphate synthetase and nucleoside diphosphate kinase in a sufficient concentration to catalyze the production of adenosine triphosphate from about picogram to microgram amounts of DNA.

The present invention provides various kits for nucleic acid detection. First, a kit is provided which contains reagents for the detection of DNA by pyrophosphorolysis. The kit contains a vessel containing a nucleic acid polymerase and a vessel containing a nucleoside disphosphate kinase. The nucleic acid polymerase and nucleoside diphosphate kinase may be provided in the same container. Second, a kit is provided which contains reagents for the detection of nucleic acid by nuclease digestion. The kit contains a vessel containing phosphoribosylpyrophosphate synthetase and a vessel containing a nuclease. Third, a kit is provided which contains reagents for the detection of RNA by pyrophosphorolysis. The kit contains a vessel containing poly(A)-polymerase. Fourth, a kit containing reagents for the detection of DNA by nuclease digestion is provided. This kit contains a vessel containing phosphoribosylpyrophosphate synthetase and a vessel containing nucleoside disphosphate kinase. The phosphoribosylpyrophosphate synthetase and nucleoside diphosphate kinase may optionally be provided in the same container.

An embodiment of the present invention further provides a kit containing reagents for the detection of cells and/or cellular material in a sample. The kit contains a vessel containing adenosine 5'-monophosphate and a vessel containing a high energy phosphate donor which may not be utilized by luciferase.

The present invention also provides a method of amplifying a nucleoside triphosphate molecule in a reaction containing adenosine 5'-monophosphate molecules, high energy phosphate donor molecules, or a combination thereof. In this method, the terminal 5' phosphate group from a nucleoside triphosphate molecule (XTP) present in the sample is enzymatically transferred to an adenosine 5'-monophosphate molecule added to the sample to form adenosine 5'-diphosphate molecules and nucleoside diphosphate molecules (XTP, either a ribonucleoside or deoxyribonucleoside triphosphate) according to the following reaction:

XTP+AMP→XDP+ADP catalyzed by a first enzyme which may be either nucleoside monophosphate kinase or adenylate kinase. Next, a phosphate from a high energy phosphate donor molecule which may not be utilized by the first enzyme is enzymatically transferred to the adenosine 5'-diphosphate molecules to form adenosine 5'-triphosphate molecules according to the following reaction:

ADP+D-P→ATP+D catalyzed by nucleoside diphosphate kinase or pyruvate kinase. These two steps are then repeated until the desired level of amplification is achieved. The high energy phosphate donors may be either dCTP or AMP-CPP for NDPK and PEP for pyruvate kinase.

The present invention also provides a method for detecting deoxyribonucleic or ribonucleic acid in a reaction containing pyrophosphate, adenosine 5'-monophosphate, and a high energy phosphate donor, or a combination thereof, in a single pot reaction. First, nucleic acid is depolymerized at a terminal nucleotide by enzymatically cleaving the terminal internucleotide phosphodiester bond with a pyrophosphate molecule to form a free ribonucleoside (XTP) or deoxynucleoside triphosphate molecule (XTP) according to reaction 1:

NA+PP$_i$→NA$_{n-1}$+XTP catalyzed by a polymerase. The depolymerizing step is repeated to obtain at least two nucleoside triphosphate molecules. The ribonucleoside triphosphate molecules or deoxyribonucleoside triphosphate molecules are then amplified by enzymatically transferring the terminal 5' phosphate group from the nucleoside triphosphate molecule formed in reaction 1 to an adenosine 5'-monophosphate to produce an adenosine 5'-diphosphate molecule and a nucleoside 5'-diphosphate molecule (XDP) according to reaction 2 catalyzed by a first enzyme:

XTP+AMP→XDP+ADP.

Next, a phosphate group from a high energy phosphate donor molecule, which is not a substrate for the first enzyme, is enzymatically transferred to the adenosine 5'-diphosphate molecules produced in a reaction to produce adenosine 5'-triphosphate molecules according to reaction 3 catalyzed by a second enzyme:

ADP+D-P→ATP+D.

The two amplification steps are repeated until the desired level of amplification is achieved. Enzyme 1 in this method may be either adenylate kinase or nucleoside monophosphate kinase, while enzyme 2 may be either pyruvate kinase or nuceloside diphosphate kinase.

DESCRIPTION OF THE PREFERRED EMBODIMENT

The present invention provides a method for detecting extremely low levels of various nucleic acids including both deoxyribonucleic acid (DNA) and ribonucleic acid (RNA) in biological samples, especially samples of recombinant proteins. The extreme sensitivity, reproducibility, ease of conducting the reactions, and speed of conducting the reactions represent major advantages over methods currently in use for low level detection of nucleic acids.

The detection method may be divided into three general steps. The first step is the production of the following nucleosides: nucleoside monophosphates (XMPs) including the ribonucleoside monophosphates (NMPs) adenosine 5'-monophosphate (AMP), guanosine 5'-monophosphate (GMP), uridine 5'-monophosphate (UMP), and cytidine 5'-monophosphate (CMP); deoxyribonucleoside monophosphates (dNMPs) including deoxyadenosine 5'-monophosphate (dAMP), deoxyguanosine 5'-monophosphate (dGMP), deoxythymidine 5'-monophosphate (dTMP), and deoxycytidine 5'-monophosphate (dCMP); nucleoside triphosphates (XTPs) including the ribonucleoside triphosphates (NTPs) adenosine 5'-triphosphate (ATP), guanosine 5'-triphosphate (GTP), uridine 5'-triphosphate (UTP), and cytidine 5'-triphosphate (CTP); and the deoxyribonucleoside triphosphates (dNTPs) including deoxyadenosine 5'-triphosphate (dATP), deoxyguanosine 5'-triphosphate (dGTP), deoxythymidine 5'-triphosphate (dTTP), and cytidine 5'-triphosphate (dCTP). The NMPs and dNMPs are produced by nuclease digestion and the NTPs and dNTPs by depolymerization by pyrophosphorolysis. The second step, used when the initial substrate is DNA, is the transfer of the terminal phosphate from the dNTPs to ADP to form ATP. The optional step of XTP amplification may be performed at this stage to increase the sensitivity of the detection system especially when measuring samples containing low levels of DNA in the range of 1–10 picograms of nucleic acid. The third step is detection of ATP by a suitable detection method. Examples of such detection systems are the luciferase detection system and NADH-based detection system.

Nucleic acid polymerases generally catalyze the elongation of nucleic acid chains. The reaction is driven by the cleavage of a pyrophosphate released as each nucleoside is added. Each nucleoside triphosphate has three phosphate groups linked to carbon 5 of ribose or deoxyribose. The addition of a nucleoside to a growing nucleic acid results in formation of a internucleoside phosphodiester bond. This bond is characterized in having a 3' linkage to carbon 3 of ribose or deoxyribose and a 5' linkage to carbon 5 of ribose or deoxyribose. Each nucleoside is added through formation of a new 3' linkage, so the nucleic acid strand grows in a 5' to 3' direction. The 5' end of the nucleic acid is characterized by a phosphate group attached to carbon 5.

Several polymerases are also known to catalyze the reverse of the polymerization process. This reverse reaction is called pyrophosphorolysis. The pyrophosphorolysis activity of DNA polymerase was demonstrated by Deutscher and Kornberg, Enzymatic Synthesis of Deoxyribonucleic Acids, J. Biol. Chem. 244: 3019–28 (1969). Other nucleic acid polymerases capable of pyrophosphorolysis include DNA polymerase α, DNA polymerase β, T4 DNA polymerase, Taq polymerase, Klenow fragment, AMV reverse transcriptase, and MMLV reverse transcriptase. However, not all polymerases are known to possess pyrophosphorolysis activity. For example, poly(A) polymerase has been reported to not catalyze pyrophosphorylation. (See Sippel, Eur. J. Biochem. 37:31–40 (1973).)

A mechanism of pyrophosphorolysis has been suggested for RNA polymerase. It is believed that the partial transfer of a $Mg^{2+}$ ion from the attacking pyrophosphate to the phosphate of the internucleoside phosphodiester bond of the RNA may increase the nucleophilic reactivity of the pyrophosphate and the electrophilicity of the diester as described in Rozovskaya et al. Biochem. J. 224: 645–50 (1984). The internucleoside phosphodiester bond is enzymatically cleaved by the addition of pyrophosphate to the nucleoside 5' phosphate and a new phosphodiester bond is formed between the pyrophosphate and the nucleoside monophosphate.

The pyrophosphorolysis reaction can be summarized as follows:

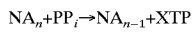  Reaction 1 wherein NA is a nucleic acid, $PP_i$ is pyrophosphate and XTP is either a deoxyribonucleoside triphosphate molecule or a ribonucleoside triphosphate molecule. The reaction may then be repeated to obtain at least two XTP molecules. It should be noted that the reaction may be repeated on the same nucleic acid molecule or on a plurality of different nucleic acid molecules.

Preferred reaction mixes for depolymerization by pyrophosphorolysis, including suitable buffers for each nucleic acid polymerase analyzed are disclosed in the Examples. Under these conditions, sufficient NTP or dNTP is produced to accurately detect or assay extremely low amounts of nucleic acids (5–15 picograms.)

Even though the preferred reaction conditions for polymerization and depolymerization by pyrophosphorolysis are similar, the rates of these reactions vary greatly. For example, AMV and RLV reverse transcriptases catalyze pyrophosphorolysis under optimal conditions at a rate of about fifty- to one hundred-fold less than polymerization as demonstrated in Srivastavan and Modak, J. Biol. Chem. 255(5): 2000–04 (1980). Thus, the high eficiency of the pyrophosphorolysis reaction was unexpected and appears to be asscociated with extremely low levels of DNA substrate in contrast to previous DNA pyrophosphorolysis studies conducted on much higher amounts of DNA.

The pyrophosphorolysis activity of different nucleic acid polymerases also varies. T4 polymerase appears to possess the greatest pyrophosphorolysis activity as measured by a luciferase assay for ATP produced by pyrophosphorolysis. Pyrophosphorolysis using T4 polymerase resulted in about a 10 fold increase in light production as compared to MMLV-RT and a 4 fold increase in light production as compared to Taq polymerase.

The detection of nucleic acids at low picogram levels is generally enhanced by fragmenting or partially digesting the nucleic acid. Preferably, fragmentation is accomplished by sonication or restriction enzyme digestion of the nucleic acid, forming a plurality of smaller nucleic acid fragments. This step probably enhances detection because the pyrophosphorolysis reaction only proceeds from the DNA ends, as demonstrated in the Examples. Providing a greater number of DNA ends means that more reactions are occurring at any one time. It should be noted that DNA ends may be present within a molecule as well as at the end of a linear DNA fragment. For example, polymerases may catalyze pyrophosphorolysis from a gap in a DNA segment or a nick in a DNA segment. The type of enzyme used for pyrophosphorolysis and the type of substrate determine whether fragmentation is necessary. For instance, the data set forth in the Examples demonstrate that fragmenting greatly increases detection of plasmid DNA when Tag polymerase is used, but does not effect detection when T4 polymerase is used. However, when chromosomal DNA is the substrate, fragmentation increases detection from both enzymes.

The type of cut made by restriction enzyme digestion also affects the pyrophosphorolysis activity of different nucleic acid polymerases. For example, MMLV-RT and Tag polymerase can catalyze pyrophosphorolysis of DNA fragments with 5' overhangs, but not 3' overhangs. In contrast, T4 DNA polymerase catalyzes both 3' and 5' end overhang and blunt end mediated pyrophosphorolysis. T4 polymerase is thus a preferred enzyme for pyrophosphorolysis. When other nucleic acid polymerases are utilized for pyrophosphorolysis of restriction enzyme treated DNA, care must be taken to match the overhang specificity of the polymerase with the type of overhang created by the restriction endonuclease.

It must be noted that sequence specificity of pyrophosphorolysis for single stranded DNA has been previously noted during sequencing by Tabor and Richardson, J. Biol.

Chem. 265 (14): 8322–28 (1990). The sequence specificity of the pyrophosphorolysis reaction was noted when some dideoxynucleoside terminated sequence fragments were shown to be more susceptible to degradation by phosphorolysis than other fragments.

Further, the type of polymerase used in the pyrophosphorolysis reaction must be matched to the correct nucleic acid substrate. In general, DNA polymerases and reverse transcriptases are preferred for depolymerizing DNA, and RNA polymerases are preferred for depolymerizing RNA. Reverse transcriptases are preferred for depolymerizing RNA-DNA hybrids.

Applicants have further demonstrated that poly(A) polymerase may catalyze pyrophosphorolysis, even though no such reaction has been previously reported. In fact, poly(A) polymerase has been widely reported to not catalyze pyrophosphorolysis. See, for example, Sippel, Eur. J. Biochem. 37:31–40 (1973) and Sano and Feix, Eur J. Biochem. 71:577–83 (1976). Surprisingly, the applicants show that under the proper reaction conditions poly(A) polymerase catalyzes phosphorolysis. Preferably, the manganese chloride present in the previously reported buffers is omitted, the concentration of sodium chloride is decreased, and the pH is lowered from about 8.0 to about 7.5. Most preferably, poly(A) polymerase pyrophosphorolysis reaction buffer contains about 50 mM Tris-Cl pH 7.5, 10 nmM $MgCl_2$, 50 mM NaCl, and 2 mM $NaPP_i$ (sodium pyrophosphate).

It is important to note that the depolymerization reaction is the reverse of the polymerization reaction. Therefore, as increasing amounts of free nucleoside triphosphates are produced by depolymerization, a state of equilibrium may theoretically be attained in which polymerization and depolymerization reactions are balanced. Alternatively, where small amounts of nucleic acid are detected, the reaction may go essentially to completion without reaching equilibrium, i.e. the nucleic acid depolymerized into its constituent subunits nucleotides by greater than 90%. This is important in a quantitative test because the total amount of nucleotides released is proprtional to the amount of signal generated in the detection assay. When used for qualitative detection of nucleic acid, it is not necessary that the reaction reach equilibrium or go essentially to completion provided a threshold level of nucleotides are produced. The mixture of nucleoside triphosphate molecules produced by depolymerization will preferably be converted to adenosine triphosphate as described below. For either detection or assay, a detectable threshold level of $6 \times 10^7$ adenosine triphosphate molecules must be provided for detection of light from a typical luciferase assay.

In a preferred embodiment of the present invention for detecting nucleic acids, nucleic acid polymerase and $PP_i$ are added to a sample containing less than 1 μg nucleic acid, down to less than about 10 pg of nucleic acid. To increase the sensitivity of the DNA detection, the DNA may be fragmented by treatment with a restriction endonuclease or by sonication. Next, the nucleic acid is degraded by pyrophosphorolysis releasing free NTPs or dNTPs. Enzymes useful in the pyrophosphorolysis reaction include AMV reverse transcriptase, MMLV reverse transcriptase, DNA polymerase alpha and beta, Taq polymerase, T4 DNA polymerase, Klenow fragment and poly(A) polymerase. Most preferably, T4 polymerase is utilized for DNA pyrophosphorolysis reactions because of its recognition of 3' and 5' overhangs and blunt ends and high processivity as noted above.

Luciferase, which is part of the preferred ATP detection system, is inhibited by pyrophosphate ($PP_i$). Therefore, care must be taken not to transfer a highly inhibiting amount of $PP_i$ to the ATP detection reaction. Preferably, the amount $PP_i$ carried over to the ATP detection reaction results in a concentration of $PP_i$ in the luciferase detection reaction of less than about 100 μM, although less than about 10 μM is desirable. Therefore, the amount of $PP_i$ utilized in the pyrophosphorolysis reaction will be determined by the size of the aliquot which is taken for use in the luciferase detection system. The aliquot size may vary, but the amount of $PP_i$ transferred or carried over to the luciferase detection reaction should correspond to the $PP_i$ concentration parameters described above so that the concentration of $PP_i$ is at least below about 100 μM, and preferably below about 10 μM.

In another embodiment, the nucleic acids may be first degraded into NMP or dNMP by exonuclease digestion according to the following reaction:

$$NA_n + H_2O \rightarrow NA_{n-1} + XMP \qquad \text{Reaction 2}$$

wherein NA is a nucleic acid, XMP is either a deoxyribonucleoside monophosphate or ribonucleoside monophosphate, and n is the number of nucleosides in the nucleic acid.

Nuclease digestion may be accomplished by a variety of nucleases including S1 nuclease, nuclease BAL 31, mung bean nuclease, exonuclease III and ribonuclease H. Nuclease digestion conditions and buffers may be found in the Product Literature available from commercial sources, or as disclosed in the Examples.

After digestion with the nuclease, the NMPs or dNMPs are converted to NTPs or dNTPs respectively. U.S. Pat. No. 4,375,897 describes the detection of RNA by digestion with nucleases followed by conversion to NTP. This method utilizes a two-step scheme in which adenylate kinase converts AMP to ADP, and pyruvate kinase then converts ADP to ATP. This method is essentially limited to the detection of poly(A) MRNA because no mechanism is suggested for conversion of dNTPs to ATP, the preferred substrate for luciferase. Nuclease digestion or phosphorolysis of DNA results in a mixture of dNTPs which do not act as efficient substrates for luciferase.

In the biosynthesis of purine and pyrimidine mononucleosides, phosphoribosylpyrophosphate (PRPP) is the obligatory ribose-5'-phosphate donor. PRPP itself is formed in a reaction catalyzed by PRPP synthetase through the transfer of pyrophosphate from ATP to ribose-5-phosphate. This reaction is known to be reversible as described in Sabina et al., Science 223: 1193–95 (1984).

In the present invention, the NMP or dNMP produced by nuclease digestion is preferably converted directly to NTP or dNTP by the enzyme PRPP synthetase in the following reactions:

$$XMP + PRPP \rightarrow XTP + \text{ribose-5-}PO_4 \qquad \text{Reaction 3}$$

wherein XMP is either adenosine monophosphate or deoxyadenosine monophosphate and XTP is either a adenosine triphosphate or deoxyadenosine triphosphate. Preferably, this reaction produces a detectable threshold level of at least $6 \times 10^7$ adenosine triphosphate molecules.

In this reaction, the pyrophosphate group of PRPP is enzymatically transferred to XMP molecules, forming XTP molecules. Reaction conditions and buffers are set forth in the Examples. When RNA is the substrate, the ATP produced may be directly detected.

Utilization of the PRPP reaction in the nucleic acid detection system has several advantages over the prior art.

First, only one step is necessary to convert an AMP or dAMP to a ATP or DATP, which simplifies the detection system. Second, contamination of the detection reaction with exogenous ATP, ADP, or AMP is less likely.

The dNTPs produced by pyrophosphorolysis or nuclease digestion followed by pyrophosphorylation can theoretically be used directly as substrates for luciferase, allowing detection of the nucleic acid. However, the preferred substrate for luciferase is ATP as demonstrated by Moyer and Henderson, Nucleoside Triphosphate Specificity of Firefly Luciferase, Anal. Biochem. 131:187–89 (1983). When DNA is the initial substrate, a nucleoside diphosphate kinase (NDPK) is conveniently utilized to catalyze the conversion of dNTPs to ATP by the following general reaction:

dNTP*+ADP→dNDP+ATP*  Reaction 4 wherein dNTP is a mixture of deoxyribonucleoside triphosphates and dNTP is the corresponding deoxyribonucleoside triphosphate. In the reaction, the terminal 5'-triphosphate (P*) of the dNTP is transferred to ADP to form ATP.

Enzymes catalyzing this reaction are generally known as nucleoside diphosphate kinases (NDPK). NDPKs are ubiquitous, relatively nonspecific enzymes. For a review of NDPK, see Parks and Agarwal, in The Enzymes, Volume 8, P. Boyer Ed. (1973). The conversion of NTPs or dNTPs to ATP by NDPK is preferably accomplished by adding NDPK and a molar excess of ADP over the amounts of NTPs or dNTPs expected to be produced by pyrophosphorolysis, or nuclease digestion followed by is pyrophosphorylation by PRPP synthetase. Alternatively, if an amplification scheme is used, a molar excess of AMP may be used as the preferred substrate. The utilization of ADP requires optimization of the amount of ADP added. Too much ADP results in high background levels. A reaction containing NDPK contains about 0.01 to 0.50 μM ADP, preferably about 0.05 μM ADP. Illustrative buffers and reaction components are set forth in the Examples.

As an optional step, the NTP, dNTP, or ATP generated by the pyrophosphorolysis or nuclease digestion schemes may be amplified to give even greater sensitivity. Amplification may be required when utilizing detection systems other than luciferase or when increased levels of signal are needed for detection by a less sensitive luminometer. Amplification of NTP means a continuous reaction wherein 1 NTP gives rise to 2 NTPs, which can be cycled to yield 4 NTPs and so on. When AMP is added to feed the amplification reaction, ATP will accumulate while the amount of original NTP remains the same. PCT publication WO 94/25619 and Chittock et al., Anal. Biochem., 255:120–6 (1998), incorporated herein by reference, disclose amplification systems for ATP characterized by the following coupled reactions:

C1+S1→2C2 and 2C2+2→2C1

2C1+2S1→4C2 and 4C2+4S2+E2→4C1

4C1+4S1→8C2 and 8C2+8S2+E2→8C1  Reaction 5 wherein C1 is the target compound present in a sample to be amplified, S1 is the amplification substrate, E1 is a catalytic enzyme capable of utilizing C1 and S1 to produce C2, S2 is an energy donating substrate, and E2 is a catalytic enzyme capable of utilizing C2 and S2 to produce C1, which then recycles through the reaction. According to this reaction scheme, each pass through the coupled reaction doubles the amount of C1, which can be subsequently detected. Patent Application GB 2,055,200 discloses an amplification system utilizing adenylate kinase and pyruvate kinase.

In designing a coupled ATP amplification reaction for use in nucleic acid detection, two main requirements must be considered. First, E1 must not be able to utilize the high energy phosphate donor utilized by E2. If E1 can utilize the high energy phosphate donor, the ATP amplification reaction would proceed in the absence of NTP or dNTP produced as a result of pyrophosphorolysis or nuclease digestion followed by pyrophosphorylation. This would result in the undesirable occurrence of false positive results. Second, a molar excess of the added high energy phosphate donor must be provided as compared to the amount of dXTP or XTP expected in the reaction. Third, E1 must be able to utilize either the NTP, dNTP, or ATP produced in step 1 by pyrophosphorolysis or nuclease digestion of the nucleic acid.

The amplification system of the present invention may be characterized, as follows:

XTP+AMP→XDP+ADP

ADP+D-P→ATP  Reaction 6 wherein D–P is a high energy phosphate donor and E1 and E2 are enzymes capable of catalyzing the transfer of phosphates from an XTP to AMP and from the D–P to ADP, respectively. The ATP so produced may reenter the reaction (as XTP) and the reaction repeated until the substrates are exhausted or equilibrium is reached, resulting in the production of two ATPs for every ATP supplied to or generated by the reaction. Note that when the target XTP is any nucleoside triphosphate other than ATP the initial pass through the cycle yields only 1 ATP which then reenters the cycle to produce two ATP, which reenter the cycle to produce 4 ATP and so on. Preferably, the amplification reaction produces a detectable threshold level of $6 \times 10^7$ adenosine triphosphate molecules.

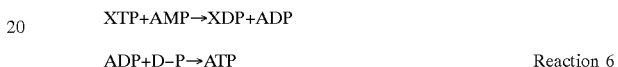

The XTP in reaction 6 is a ribonucleoside triphosphate or deoxyribonucleoside triphosphate, which may preferably be ATP provided by pyrophosphorolysis (Reaction 1) or created from XTP by NDPK conversion of ADP to ATP (Reaction 5) or provided by nuclease digestion coupled with pyrophosphorylation (Reaction 4) followed by NDPK conversion to ATP (Reaction 5). It must be appreciated, however, that when an amplification step is utilized for a DNA substrate, the step of converting dNTP to ATP is inherent in the amplification system. Therefore, a separate converting step is not needed.

A nucleoside monophosphate kinase (NMPK) or adenylate kinase is preferably utilized as enzyme 1 (E1). NMPKs occur as a family, each of which is responsible for catalyzing the phosphorylation of a particular NMP. Until recently, it was generally thought that ATP and DATP were preferred phosphate donors. However, Shimofuruya and Suzuki Biochem. Intl. 26(5):853–61 (1992) recently demonstrated that at least some NMPKs can utilize other phosphate donors such as CTP and UTP. Enzyme 2 (E2) is preferably nucleoside diphosphate kinase (NDPK) or pyruvate kinase. NDPK's generally catalyze the transfer of the terminal 5'-triphosphate of NTPs to NDPs to form NTPs. Pyruvate kinase catalyzes the transfer of phosphate from phosphoenolpyruvate to ADP to form ATP. These enzymatic activities are utilized in the amplification reaction to transfer a phosphate group from a high energy phosphate donor (D–P) to either ADP or an NDP.

A high energy phosphate donor (D–P) that may be used by E2 but not by E1 is required. When E2 is NDPK, dCTP or α, β methylene adenosine 5'-triphosphate (AMP-CPP)

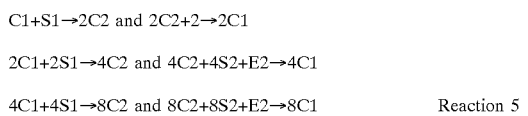

may be utilized as D–P. When E2 is pyruvate kinase, phosphoenol pyruvate (PEP) is the preferred high energy phosphate donor. The ability of NDPK to utilize these substrates at efficiencies allowing production of minute quantities of ATP was not known. It is surprising that these high-energy phosphate donors utilized with NMPK and adenylate kinase meet the requirements of the amplification reaction when the recent literature suggests that NMPK (E1) may utilize phosphate donors other than ATP or dATP. The nonspecificity of adenylate kinase is also well known. The high energy phosphate donor and/or AMP must be provided in a molar excess as compared to the amount of ATP or dNTP expected present in the sample so that the high energy phosphate donor is not recycled at an appreciable rate. Additional buffers and reaction components are included in the Examples.

The third step of nucleic acid detection is detection of the NTP, dNTP or amplified ATP. Two well known detection systems include: the light emitting luciferase detection system, and the NADH light adsorption detection system (NADH detection system).

The ATP so produced is detected by a luciferase detection system. In the presence of ATP and O2, luciferase catalyzes the oxidation of luciferin, producing light which can then be quantitated using a luminometer. Additional products of the reaction are AMP, pyrophosphate and oxyluciferin. The light can be detected by a luminometer.

The preferred ATP detection buffer, which will be referred to as LAR buffer, is formulated by mixing 19.1 ml of deionized water; 800 $\mu$l of 0.5M Tricine, pH 8.0; 70 $\mu$l of 1M MgSO$_4$; 4 $\mu$l of 0.5M EDTA; 0.108g of DTT (dithiothreitol); 0.003 g of Luciferin; and adjusting the pH to 7.8 if necessary. Preferably, about 5 to 10 nanograms of recombinant luciferase (Promega Lot 6414002) is used in the reaction. Greater amounts of luciferase have a tendency to increase non-specific background. Applicants also have shown that deleting coenzyme A from the LAR reaction mix decreases background.

In the NADH detection system, a combination of two enzymes, phosphoglycerate kinase and glyceraldehyde phosphate dehydrogenase, are used to catalyze the formation of NAD from NADH in the presence of ATP. ATP is measured as a loss in fluorescence intensity because NADH is fluorescent while NAD is not. Examples of NADH based ATP assays are disclosed in U.S. Pat. Nos. 4,735,897, 4,595,655, 4,446,231 and 4,743,561, and UK Patent Application GB 2,055,200, all incorporated herein by reference.

Certain of the above reactions may be performed as single pot reactions. A single pot reaction is a reaction wherein at least two enzymes (E1 and E2) with catalytic activity are present in the same reaction mix and act on one or more substrates) (S1 and S2). The reactions catalyzed by the enzymes may occur simultaneously where E1 acts on S1 and E2 acts on S2 successfully. Alternatively, the reactions catalyzed by E1 and E2 may occur in a step-wise or coupled manner where E1 acts on S1 to produce an intermediate $S2_i$ and E2 then acts on $S2_i$. Of course, such a coupled reaction may also be essentially simultaneous.

The ability to utilize combinations or mixtures of the enzymes of the present invention in single pot reactions is surprising in light of the extremely low levels of nucleic acid detection which are achieved. This low level detection is possible even though some enzymes are used under less than optimal conditions. As previously described, it was necessary to optimize the concentration of $PP_i$ utilized in the pyrophosphorolysis reactions so that luciferase would not be inhibited. Therefore, aliquots from the NMP, dNMP, NTP, dNTP and ATP producing reactions may be directly added to LAR buffer for luciferase detection without any purification of the reaction products. The luciferase reaction is not poisoned or otherwise quenched by the components of the reactions. This desirable feature allows high throughput screening with a minimal amount of time and effort, and also allows great flexibility in the design of the overall detection schemes.

Preferably, the pyrophosphorolysis reaction producing dNTP and the NDPK catalyzed reaction in which the NTPs or dNTPs are converted to ATP may be performed in a single pot reaction in the nucleic acid polymerase buffer. NDPK activity is sufficient to convert dNTP to ATP even though the polymerase buffer conditions are suboptimal for NDPK activity. The polymerase enzyme and NDPK may both be present initially in the reaction, or the NDPK may be added directly to the reaction after an incubation period sufficient for the production of NTP or dNTP. A nucleic acid polymerase and NDPK may be provided in the same vessel or mixture for use in the reactions described above. The mixture preferably contains the nucleic acid polymerase and NDPK in a concentration sufficient to catalyze the production of ATP when in the presence of a nucleic acid, pyrophosphate and ADP. Preferably, the polymerase is provided in a concentration of about 1 to 100 units/$\mu$l, most preferably at about 5 units/$\mu$l. Preferably, the NDPK is provided in a concentration of 0.1 to 100 units/$\mu$l, most preferably at about 5 units/$\mu$l. Preferably, the mixture is greater than 99% pure.

Similarly, the PRPP synthetase and NDPK reactions can be performed in a single pot reaction in the PRPP synthetase buffer. Again, NDPK activity is sufficient even though conditions for NDPK activity are suboptimal. The nuclease digested sample containing free NMPs and dNMPs may be added to a reaction mix initially containing PRPP synthetase and NDPK, or added to a PRPP synthetase reaction followed by addition to a reaction mix containing NDPK and the luciferase detection reaction components. The preferred buffers and reaction components may be found in the Examples. PRPP synthetase and NDPK may be provided in the same vessel or mixture for use in the reactions described above. The mixture preferably contains the PRPP synthetase and NDPK in a concentration sufficient to catalyze the production of ATP when in the presence of phosphoribosylpyrophosphate and ADP. Preferably, the NDPK is provided in a concentration of 0.1 to 100 units/$\mu$l, most preferably at about 5 units/$\mu$l. Preferably, the PRPP synthetase is provided in a concentration of 0.001 to 10 units/$\mu$l, most preferably at about 0.01 units/$\mu$l If amplification is desired, the PRPP synthetase reaction must be heat inactivated, otherwise the PRPP synthetase would convert the added AMP to ATP. Preferably the mixture is greater than 99% pure.

The pyrophosphorolysis reaction and amplification reaction may also be performed in a single pot reaction. In this single pot reaction, the polymerases may be AMV reverse transcriptase, MMLV reverse transcriptase, DNA polymerase alpha or beta, Taq polymerase, T4 DNA polymerase, Klenow fragment or poly(a) polymerase, a first enzyme for converting AMP to ADP may be myokinase (adenylate kinase) or NMPK, and a second enzyme for converting ADP to ATP may be pyruvate kinase or NDPK. The reaction must be fed AMP, preferably Apyrase treated AMP so that background due to contaminating ADP and ATP is minimized. Preferably 1$\mu$l of 1U/$\mu$l Apyrase may be added to 19 $\mu$l of 10 mM AMP, followed by incubation at room temperature for 30 minutes and heat inactivation of the Apyrase by incubation at 70° C. for 10 minutes. High energy phosphate donors must also be added to the reaction. When pyruvate kinase is utilized phosphoenolpyruvate is added, while when NDPK is utilized dCTP is added. Preferably, the high energy phosphate donor is added about 15 minutes after a preincubation with the polymerase, although this is not necessary. These reactions may characterized as follows:

$$NA_n+PP_i \rightarrow NA_{n-1}+XTP$$

$$XTP+AMP \rightarrow ADP+XDP$$

$$ADP+D-P \rightarrow ATP+D \qquad \text{Reaction 7}$$

wherein NA is a nucleic acid, XTP is a nucleoside triphosphate, either a deoxynucleoside or ribonucleoside triphosphate, XDP is a nucleoside diphosphate, either a deoxynucleoside or ribonucleoside diphosphate, and D–P is a high energy phosphate donor. It should be appreciated that this reaction produces ATP, the preferred substrate for luciferase, from dNTPs. The amplification reaction proceeds as described in reaction 7 to produce a detectable threshold level of $6 \times 10^7$ adenosine triphosphate molecules. Preferably, the polymerase is provided in a concentration of about 1 to 100 units/$\mu$l, most preferably at about 5 units/$\mu$l. Preferably, the NDPK is provided in a concentration of 0.1 to 100 units/$\mu$l, most preferably at about 1 unit/$\mu$l. Preferably, the Preferably, the mixture is greater than 99% pure.

In another embodiment, the reactions described above may be used to selectively detect poly(A) mRNA according to the following scheme. First oligo(dT) primers are hybridized to the poly(A) tails of the mRNA to form a DNA-RNA hybrid. Next, a pyrophosphorolysis reaction is performed using reverse transcriptase (RT). Reverse transcriptases which may be used in the present invention include Mouse Mammary Leukemia Virus (MMLV) RT, Avian Myeloma Virus (AMV) RT and Rous Sarcoma Virus (RSV) RT. An advantage of this detection system is that these RTs catalyze pyrophosphorolysis of double stranded nucleic acid and double stranded RNA-DNA hybrids, but not single stranded nucleic acids. Thus, the amount of poly(A) RNA in a total cellular RNA sample be determined. The pyrophosphorolysis reaction produces dTTP according to the following reaction:

$$TT_n+PP_i \rightarrow TT_{n-1}+dTTP; \qquad \text{Reaction 8}$$

wherein $TT_n$ is oligo(dT) and $PP_i$ is pyrophosphate.

The dTTP can be converted to ATP by NDPK as described in reaction 4 above, optionally amplified, and detected as described above.

In another embodiment, the reactions described above may be used to detect the presence of cells in a sample. U.S. Pat. No. 5,648,232, incorporated herein by reference, describes a method of detecting cells in a sample. That method takes advantage of adenylate kinase activity, which is present in all living organisms. Briefly, a sample suspected of containing microorganisms or other living cells is subjected to conditions causing cell lysis. ADP is then added to the lysate, which is converted by endogenous adenylate kinase activity to ATP by the following reaction:

$$ADP+ADP \rightarrow ATP+AMP \qquad \text{Reaction 9}$$

The ATP produced by this reaction is then detected by the luciferase assay system.

The present invention also provides a method of detecting the presence of cells in a lysate of a sample suspected of containing cellular material by using different substrates. This system takes advantage of a coupled reaction catalyzed by endogenous adenylate kinase activity (AK) and NDPK activity according to the following reaction scheme:

$$AMP+D-P \rightarrow D+ADP \text{ and}$$

$$ADP+D-P \rightarrow ATP+D. \qquad \text{Reaction 10}$$

wherein D–P is a high energy phosphate donor added to the cell lysate and AMP is adenosine monophosphate added to the cell lysate sample. In this reaction, adenosine 5'-diphosphate molecules are produced by the enzymatic transfer of a phosphate group from the high energy phosphate donor molecules (D–P) to the added adenosine 5'-monophosphate (AMP) molecules. Then, adenosine 5'-triphosphate is produced by the enzymatic transfer of phosphate from D–P molecules to the adenosine 5'-diphosphate molecules according to the following general reaction catalyzed by endogenous enzymes present in the cell lysate sample Co-optimization of the concentrations of nucleosides added to the samples was necessary to optimize light output from these reactions. About 1 mM to 80 mM AMP and 1 mM to 100 mM dCTP may be added to the test sample, and preferably about 10 mM AMP and 100 mM dCTP may be added to the test sample. After addition of nucleosides to the sample, the samples are preferably incubated at room temperature for about 10 to 60 minutes, and light output from the samples determined by a luminometer. Other preferred buffers and reactions components may be found in the Examples.

This system has an important advantage over previously described cell detections systems. The AMP and dCTP are much more stable than ADP, so the results are more reproducible.

In another aspect of the present invention, a nucleic acid detection test kit is provided for performing the pyrophosphorolysis nucleic acid detection method. The nucleic acid detection test kit comprises the essential reagents required for the method of the nucleic acid detection invention. For nucleic acid detection by pyrophosphorolysis, the kit includes a vessel containing an enzyme capable of catalyzing pyrophosphorolysis such as Taq polymerase, T4 polymerase, AMV reverse transcriptase, MMLV reverse transcriptase, or poly(A) polymerase. The concentration of polymerase is 0.1 to 100 units/$\mu$l, preferably about 5 units/$\mu$l. Kits for use in DNA detection also include a vessel containing nucleoside diphosphokinase and a vessel containing ADP. Preferably, these reagents are free of contaminating ATP and adenylate kinase. The NDPK is provided in concentration of about 0.1 to 100 units/$\mu$l, preferably about 1.0 units/$\mu$l. The contaminants may be removed by dialysis or Apyrase treatment. Optionally, the kit may contain vessels with reagents for amplification of dNTPs or NTP to ATP. Amplification reagents include pyruvate kinase, adenylate kinase, NMPK, NDPK, AMP as the amplification substrate, and dCTP or AMP-CPP as high-energy phosphate donors. The kit may be packaged in a single enclosure including instructions for performing the assay methods. The reagents are provided in containers and are of a strength suitable for direct use or use after dilution. A standard set may also be provided to allow quantitation of results. Test buffers for optimal enzyme activity may be included. Most preferably, the NDPK and nucleic acid polymerase are provided in the same reaction mix so that a single pot reaction may be performed consistently.

In another aspect of the present invention, a nucleic acid detection kit is provided for performing the nuclease digestion nucleic acid detection method of the present invention. This test kit comprises the essential reagents required for this method. These reagents include a nuclease, PRPP synthetase, PRPP, NDPK, and ADP together with luciferase and luciferin. The nuclease is provided in a concentration of about 1 to 500 units/μl, preferably about 20 units/μl. The PRPP synthetase is provided in concentration of about 0.01 units/μl to 10 units/μl, preferably about 0.1 units/μl. Preferably, the kit includes all these reagents with luciferase and luciferin being provided as a single reagent solution. Most preferably, the PRPP synthetase and NDPK are provided in a single reaction mix so that a single pot reaction containing these two enzymes may be performed, simplifying the detection method. The kit is in the form of a single package preferably including instructions to perform the method of the invention. The reagents are provided in vessels and are of a strength suitable for direct use or use after dilution. Preferably, buffers which support the optimal enzyme activity are provided. Optionally, reagents for amplification of the ATP signal may be provided as described in the previous kit.

In another aspect of the present invention, a test kit is provided for determining the presence of microorganisms or other cells in a test sample. This test kit comprises the essential reagents required for the method. These reagents include a high-energy phosphate donor which may not be utilized by luciferase, preferably dCTP, and AMP together with luciferase and luciferin. Preferably, the kit includes all these reagents with luciferase and luciferin being provided in the same solution. Preferably, the reagents are free of contaminating components such as adenylate kinase and ATP that would cause a false positive test. A cell lysis cocktail may be provided for efficiently releasing the contents of the target cells for each of the assays intended. For prokaryotic microorganisms, only a cationic detergent is needed. For fungal spores or eukaryotic cells assays, a further nonionic detergent reagent is included. Reagents are provided in vessels and are of a strength suitable for direct use or use after dilution. A buffer solution for diluting the cell samples may also be provided.

Other aspects of the present invention will be made apparent in the following examples. These Examples are intended to illustrate the invention and in no way limit any aspect of the invention.

EXAMPLES

Example 1
Detection of ATP Using Luciferase

The ultimate sensitivity of detection using an enzyme based detection system is related to the ability of the enzymatic reaction to produce a measurable signal over background. This example describes the detection of very low levels of ATP using Luciferase.

Luciferase Assay Reagent buffer (LAR) was produced by mixing: 19.1 ml of nanopure water; 800 μl of 0.5M Tricine (Sigma T9784), pH 8.0; 70 μl of 1M MgSO$_4$ (Promega AA319, Lot #970931); 4 μl of 0.5M EDTA (Promega AA189, Lot #962131); 0.13 g of DTT (dithiothreitol, Promega V31SA); 0.003 g of Beetle Luciferin (Promega E160C, Lot #79838); 0.0044 g of Coenzyme A, pH 7.8 (Pharmacia 28-3001-03 Lot #7053001031). A 0.M solution of ATP was prepared by dissolving solid ATP (Sigma A9187) in Tris 10 mM pH 7.5. This stock solution was diluted into Tris 10 mM pH 7.5 to produce solutions at 100 μM, 1 μM, 10 nM, and 100 pM. Recombinant Luciferase (Promega #1701, Lot #6414002) was diluted to 1 mg/ml, 100 μ/ml, and 10 μg/ml using nanopure water.

Reactions were assembled in duplicate containing the following components in 1.5 ml polypropylene tubes as described in Table 1.

TABLE 1

| Reaction | Components LAR | Luciferase | Total Luciferase Added |
|---|---|---|---|
| 1 | 50 ul | 1 ul of 1 mg/ml | 1 μg |
| 2 | 50 ul | 1 ul of 100 μg/ml | 100 ng |
| 3 | 50 ul | 1 ul of 10 μg/ml | 10 ng |
| 4 | 50 ul | (none) | 0 ng |

Immediately upon addition of the Luciferase, the tube was read in a Turner TD-20e Luminometer. The values obtained are listed in Table 2.

TABLE 2

| Reaction | Light Units | Light 2 | Avg. | Filter* | Total Light Units |
|---|---|---|---|---|---|
| 1 | 90.6 | 66.09 | 78.345 | 286 | 22406.67 |
| 2 | 2048 | 2096 | 2072 | none | 2072 |
| 3 | 148 | 122 | 135 | none | 135 |
| 4 | 0 | 0 | 0 | none | 0 |

*light reduction filter used to reduce signal, light units measured must be multiplied by filter to obtain light output Luciferase requires both ATP and Luciferin to produce a light signal. The light produced in the reactions above is the result of ATP contamination of either the LAR reagent or the Luciferase added to the reactions. Ten and five nanogram levels of Luciferase were chosen for further studies since they produced the lowest level of background light without ATP addition, yet were expected to give greatly increased light output upon addition of ATP.

Reactions were assembled in duplicate containing 50 μl of LAR buffer, 1 μl of stock Luciferase providing either 5 or 10 ng of luciferase to the reaction, and ATP at the concentrations listed below. Light output from reactions was then immediately determined with a Turner TD-20e Luminometer. The results are described in Table 3. These data indicate that Luciferase is capable of detecting low levels of ATP if levels of Luciferase are used that minimize the background resulting from ATP contamination of the reagent.

TABLE 3

| Luciferase (ng) | ATP Conc. | μl | Light Units | | Filter | Avg. Light Units |
|---|---|---|---|---|---|---|
| 10 | (none) | na | 131.7 | 119.6 | (none) | 125.7 |
| 10 | 100 uM | 5 | 26.09 | 25.25 | 286 | 7221.5 |
| 10 | 1 uM | 5 | 249.5 | 226.1 | (none) | 237.8 |
| 10 | 10 nM | 5 | 131.7 | 232.6 | (none) | 182.2 |
| 10 | 100 pM | 5 | 215.4 | 143.9 | (none) | 179.7 |

TABLE 3-continued

| Luciferase | ATP | | | | Avg. |
|---|---|---|---|---|---|
| (ng) | Conc. | µl | Light Units | Filter | Light Units |
| 5 | (none) | na | 52.76  50.04 | (none) | 51.4 |
| 5 | 100 uM | 5 | 17.99  18.47 | 286 | 5213.8 |
| 5 | 1 uM | 5 | 156.4  174.4 | (none) | 167.9 |
| 5 | 10 nM | 5 | 46.13  34.37 | (none) | 40.3 |

Example 2
Limit of ATP Detection Using Luciferase

This example demonstrates that the light output values obtained from reactions with very low levels of ATP are statistically different from appropriate control reactions. The limit of detection can be defined as the amount of the analyte that generates a signal which has less than a 0.05 probability of identity to the data from control reactions using the Student's t-Test.

ATP (Sigma A9187, Lot #36H7808 Promega, stored overnight at −20 degrees) in 10 mM Tris-Cl pH 7.5 was diluted to 500 nM and 50 nM. Various amounts of ATP were added to 350 µl, with Tris added to make up the difference in volume (385 total). Only Tris was added to the control to determine the background signal. After mixing, 6 aliquots of 50 µl of the control and containing samples were transferred to luminometer tubes. Luciferase (2 µl of 2.5 ng/µl in 1×CCLR with 1 mg/ml BSA (1×CCLR Promega E153A, Lot #7903201)) was added to the reaction, the tube was tapped to mix the reagents and light output was immediately determined with the Turner TD-20e luminometer. The data is presented in Table 4.

TABLE 4

| Reaction | ATP (M) | Light |
|---|---|---|
| 1 | 0 | 2.744 |
| 2 | 0 | 2.606 |
| 3 | 0 | 2.849 |
| 4 | 0 | 2.834 |
| 5 | 0 | 2.801 |
| 6 | 0 | 2.778 |
| 7 | $4.5 \times 10^{-10}$ | 4.883 |
| 8 | $4.5 \times 10^{-10}$ | 5.192 |
| 9 | $4.5 \times 10^{-10}$ | 4.945 |
| 10 | $4.5 \times 10^{-10}$ | 4.220 |
| 11 | $4.5 \times 10^{-10}$ | 5.282 |
| 12 | $4.5 \times 10^{-10}$ | 5.216 |
| 13 | $9.1 \times 10^{-10}$ | 7.167 |
| 14 | $9.1 \times 10^{-10}$ | 8.100 |
| 15 | $9.1 \times 10^{-10}$ | 7.774 |
| 16 | $9.1 \times 10^{-10}$ | 8.047 |
| 17 | $9.1 \times 10^{-10}$ | 8.010 |
| 18 | $9.1 \times 10^{-10}$ | 7.677 |
| 19 | $1.82 \times 10^{-9}$ | 10.70 |
| 20 | $1.82 \times 10^{-9}$ | 11.02 |
| 21 | $1.82 \times 10^{-9}$ | 11.93 |
| 22 | $1.82 \times 10^{-9}$ | 11.91 |
| 23 | $1.82 \times 10^{-9}$ | 12.27 |
| 24 | $1.82 \times 10^{-9}$ | 11.92 |

The Student's t-Test (a 2-tailed test for 2 samples with unequal variance) was used to analyze the data. The light output from each ATP concentration was compared to the light output of the background control, and a p-value determined for each comparison. The results of the analysis are presented in Table 5. A p-value of less than 0.05 indicates that the 2 sets of results being compared are statistically different from each other. Each of the ATP concentrations compared to background signal have a p-value of less than 0.05. Therefore, this statistical test indicates that each of the ATP concentrations analyzed is detectable over background.

TABLE 5

| | p-value |
|---|---|
| $1.82 \times 10^{-9}$ M ATP | $2.2 \times 10^{-5}$ |
| $9.1 \times 10^{-10}$ M ATP | $9.5 \times 10^{-8}$ |
| $4.5 \times 10^{-10}$ M ATP | $2.3 \times 10^{-7}$ |

Example 3
Detection of dATP Using Luciferase

Detection of polydeoxyribonucleosides using Luciferase can in theory be performed through the measurement of dATP if the enzyme used for detection can utilize dATP. In this example, the ability of Luciferase to use deoxyadenosine triphosphate (dATP) as compared to adenosine triphosphate (ATP) was tested.

Reactions were assembled containing 50 µl of LAR, 2 or 4 µl of luciferase stock (providing 5 or 10 ng of luciferase to the reactions) and 0 or 5 µl of 1 mM dATP Sigma (final concentration of dATP approximately 100 µM). Luciferase was the last component added. Immediately upon enzyme addition, the light output of the reactions was determined using a Turner TD-20e Luminometer. The results are provided in Table 6. These data show that Luciferase can be used to directly detect dATP.

TABLE 6

| Luciferase Level | dATP + or − | Light Units | | Avg. |
|---|---|---|---|---|
| 5 ng | − | 423 | 295.7 | 359.4 |
| 5 ng | + | 1450 | 1621 | 1535.5 |
| 10 ng | − | 703 | 705.5 | 704.3 |
| 10 ng | + | 3684 | 3441 | 3562.5 |

Example 4
Pyrophosphate Inhibition of Luciferase

The reaction of Luciferase produces pyrophosphate from ATP or dATP and is inhibited by pyrophosphate. Some of the reaction schemes described later use pyrophosphate as a substrate for other enzymes. In order to use levels of pyrophosphate in these reactions which do not inhibit detection of nucleoside using Luciferase, we determined the levels of inhibition produced by various concentrations of pyrophosphate on the production of light from Luciferase.

A new buffer, LAR without Coenzyme A, was made as described in Example 1. This buffer and the original LAR were then used to formulate various reactions with the compositions shown below. The reactions were assembled with Luciferase being the final component added. Immediately upon enzyme addition, the light output of the reactions were determined with a Turner TD-20e Luminometer. The results are provided in Table 7. These data indicate that the light output from Luciferase can be measured in the presence of pyrophosphate and that more than 50% of the activity can be seen with pyrophosphate concentrations as high as 100 µM. In addition, these data indicate that removal of Coenzyme A from the LAR greatly lowers the background light produced by the reactions without greatly effecting the activity of Luciferase.

TABLE 7

| LAR with CoA (µl) | LAR minus CoA (µl) | ATP (2 µM) | pp$_i$ 1 mM | pp$_i$ 100 µM | Luciferase (2.5 µg/ml) | Light Units | | Avg. |
|---|---|---|---|---|---|---|---|---|
| 50 µl | – | – | – | – | 2 µl | 209.9 | 227 | 218.5 |
| 50 µl | – | 5 µl | – | – | 2 µl | 3462 | 3674 | 3568 |
| 50 µl | – | – | + | – | 2 µl | 9.73 | 9.54 | 9.6 |
| 50 µl | – | 5 µl | + | – | 2 µl | 169.5 | 180.9 | 175.2 |
| 50 µl | – | 5 µl | – | + | 2 µl | 1452 | 1449 | 1450.5 |
| – | 50 µl | – | – | – | 2 µl | 0.035 | 0.046 | 0.041 |
| – | 50 µl | 5 µl | – | – | 2 µl | 3735 | 3289 | 3512 |
| – | 50 µl | – | + | – | 2 µl | 0.0003 | 0.0003 | 0.0003 |
| – | 50 µl | 5 µl | + | – | 2 µl | 254.5 | 308 | 281.3 |
| – | 50 µl | 5 µl | – | + | 2 µl | 2041 | 2069 | 2055 |

Example 5
Testing ADP as an Inhibitor of Luciferase

Some of the reaction schemes described later use adenosine diphosphate (ADP) as a substrate for other enzymes. ADP is a possible inhibitor of Luciferase. Therefore, we determined the levels of inhibition produced by various concentrations of ADP on the production of light from Luciferase and ATP.

Stock solutions of ADP Sigma or ATP were dissolved in 10 mM Tris-Cl pH 7.5 and diluted to produce various stock concentrations. Reactions were assembled which contained 2 µl of 2.5 µg/ml Luciferase, 50 µl of LIAR, 5 µl of ADP or 5 µl of 10 mM Tris Cl pH 7.5 and 5 µl of ATP or 5 µl of 10 mM Tris Cl pH 7.5. The Luciferase was the final component added to these reactions. Immediately upon enzyme addition, the light output of the reactions was measured using a Turner TD-20e Luminometer. The final nucleoside concentrations of the reactions and the light output of the reactions are summarized in Table 8. These data indicate that ADP does not greatly effect the ability of Luciferase to produce light using ATP as a substrate. Thus, if low concentrations of ADP are added to Luciferase reactions from reactions performed using other enzymes, little effect on ATP detection through the use of Luciferase is expected.

TABLE 8

| ATP | ADP | Light output | | Average |
|---|---|---|---|---|
| — | — | 485.8 | 423.5 | 454.7 |
| 2 µM | — | 4945 | 4930 | 4937.5 |
| — | 100 µM | 4800 | 4418 | 4609 |
| 2 µM | 100 µM | 6834 | 7207 | 7020.5 |
| — | 1 µM | 513 | 463 | 488 |
| 2 µM | 1 µM | 4303 | 4152 | 4227.5 |
| — | 10 nM | 419.6 | 419 | 419 |
| 2 µM | 10 nM | 4534 | 4625 | 4579.5 |

Example 6
NDPK Transformation of ADP to ATP, Using Deoxynucleosides

Luciferase can detect ATP at much lower concentrations than dATP or other nucleosides. If deoxynucleoside triphosphates could be used to generate ATP, an increase in sensitivity may result. For this reason, we tested the ability of enzymes to transfer the terminal phosphate of deoxynucleoside triphosphates to ADP, forming ATP and deoxynucleoside diphosphates.

Reactions were assembled which contained 100 µl of LAR, 10 ng of Luciferase in the presence or absence of deoxynucleoside triphosphates (1 µM final concentration when added), and 10 units of nucleoside diphosphate kinase (NDPK) (Sigma #N0379, Lot #127F81802). The reactions were assembled with the exception of luciferase and incubated for 15 min at room temperature. The Luciferase was added and the light output of the reactions was measured immediately using a Turner TD-20e Luminometer. The light output values measured are provided in Table 9. These data confirm that NDPK is capable of transferring the phosphate from nucleoside triphosphates to ADP to form ATP which can be detected using Luciferase.

TABLE 9

| Tube # | dNTP | ADP | NDPK | ATP | Light Units |
|---|---|---|---|---|---|
| 1 | — | + | + | | 883 |
| 2 | — | – | + | + | 15361 |
| 3 | — | + | – | | 543 |
| 4 | — | – | – | + | 21970 |
| 5 | dATP | + | + | | 13356 |
| 6 | dATP | – | + | | 151 |
| 7 | dCTP | + | + | | 13007 |
| 8 | dCTP | – | + | | 6.9 |
| 9 | dGTP | + | + | | 13190 |
| 10 | dGTP | – | + | | 7.3 |
| 11 | TTP | + | + | | 19230 |
| 12 | TTP | – | + | | 9.0 |

Example 7
NDPK Transformation of ADP to ATP Using NDPK and ATP Analogs

Some enzymes which may be used to transform nucleosides show specificity for adenosine nucleosides as phosphate donors. Adenosine nucleosides may not be used as high energy phosphate donors for these converting enzymes if a Luciferase detection system is to be utilized. This is because light would be generated by Luciferase from the added adenosine nucleoside. However, the converting enzymes may be utilized if an analog of adenosine is identified that can be used by the converting enzymes but not by Luciferase. This example indicates how such analogs can be tested for their ability to be used by converting enzymes but not by Luciferase.

Approximately 5 mg of ATP (Sigma A9187, Lot #36H7808), α,β methyleneadenosine 5'-Triphosphate (AMP-CPP) (Sigma M6517, Lot #96H7813) and β,γ methylene adenosine 5'-triphosphate (AMP-PCP) (Sigma M7510, Lot #34H7840) were diluted in Tris-Cl, 10 mM, pH 7.5. The absorbance of a 1:100 dilution of these solutions into 50 mM Tris-Cl, pH 7.5 was read at 259 nm using a Beckman DU650 Spectrophotometer. The absorbances were used to determine the concentration of these solutions using a molar extinction coefficient of 15.4×10$^3$ M. Recombinant Luciferase was diluted into CCLR containing 1 mg/ml BSA to a concentration of 2.5 ng/µl. When the reactions were assembled, 2 µl luciferase was added from the 2.5 ng/µl stock solution and the light emission of the solutions were immediately read using a Turner TD-20e Luminometer. The data is provided in Table 10.

TABLE 10

| Reaction | LAR | ATP | AMP-CMP* | AMP-PCP* | # rxn | Avg. |
|---|---|---|---|---|---|---|
| 1 | 50 µl | — | — | — | 3 | 426.4 |
| 2 | 50 µl | 4 µM | — | — | 7 | 5762 |
| 3 | 50 µl | — | 552 µM | — | 2 | 349.2 |
| 4 | 50 µl | 4 µM | 552 µM | — | 2 | 5072.5 |
| 5 | 50 µl | — | 5.52 µM | — | 2 | 465.8 |
| 6 | 50 µl | 4 µM | 5.52 µM | — | 2 | 5843.5 |
| 7 | 50 µl | — | 55.2 nM | — | 2 | 429.8 |
| 8 | 50 µl | 4 µM | 55.2 nM | — | 2 | 4152 |
| 9 | 50 µl | — | — | 1.14 mM | 2 | 260.35 |
| 10 | 50 µl | 4 µM | — | 1.14 mM | 2 | 3735.5 |
| 11 | 50 µl | — | — | 11.4 µM | 2 | 431.25 |
| 12 | 50 µl | 4 µM | — | 11.4 µM | 2 | 5930 |
| 13 | 50 µl | — | — | 114 nM | 2 | 389.35 |
| 14 | 50 µl | 4 µM | — | 114 nM | 2 | 6093.5 |

*final concentration in the reaction, solution produced by concentrated stock solution Micromolar solutions of these ATP analogs do not produce light above reactions containing no added nucleoside and do not greatly lower the light output of reactions containing low levels of ATP from the values seen in the absence of these analogs. These analogs do not inhibit Luciferase and are not utilized by Luciferase. Thus, these data indicate that these analogs can be tested for their ability to be used with enzymes for the transformation of nucleosides.

The following reactions were performed to determine if either AMP-CPP or AMP-PCP could be used by NDPK. All reactions were assembled in duplicate and incubated at room temperature for 20 min. Ten nanograms of Luciferase was added and the light output of the reactions immediately measured using a Turner TD-20e Luminometer. The data is provided in Table 11. These data demonstrate the analog AMP-CPP is utilized by the enzyme NDPK as a substrate to generate ATP from ADP. The values seen with AMP-CPP, ADP and NDPK present are substantially higher than those seen for ADP alone, ADP and NDPK without AMP-CPP and NDPK alone. Analogous experiments can be performed to test other enzymes for their ability to use nucleoside substrates in a similar fashion.

TABLE 11

| Reaction | LAR-CoA | ADP ($2 \times 10^{-4}$ M) | NDPK | AMP-CPP ($2 \times 10^{-5}$ M) | AMP-PCP ($2 \times 10^{-5}$ M) | Avg. |
|---|---|---|---|---|---|---|
| 1 | 100 µl | — | — | — | — | 0.21 |
| 2 | 100 µl | 0.5 µl | — | — | — | 60.23 |
| 3 | 100 µl | 0.5 µl | 1 µl | — | — | 59.77 |
| 4 | 100 µl | 0.5 µl | 1 µl | 5 µl | — | 617.95 |
| 5 | 100 µl | — | 1 µl | 5 µl | — | 1.81 |
| 6 | 100 µl | 0.5 µl | 1 µl | — | 5 µl | 69.35 |
| 7 | 100 µl | — | 1 µl | — | 5 µl | 0.03 |
| 8 | 100 µl | — | 1 µl | — | — | 0.05 |

Example 8
NMPK Transformations of ADP

This example demonstrates a method for testing the ability of an enzyme to transform nucleoside diphosphates into nucleosides which can be used by Luciferase for the generation of light. The enzyme Nucleoside Monophosphate Kinase (NMPK, Sigma, N-4379) can transfer the phosphate from ATP to UMP, forming UDP and ADP. This experiment demonstrates that this enzyme preparation can also be used to form ATP from ADP, probably through the reaction:

2ADP→ATP+AMP

The reactions were assembled in duplicate as prescribed in Table 12 and incubated at room temperature for 30 min. At that time, long of Luciferase was added and the light output of the solutions was measured using a Turner TD-20e Luminometer. The data is provided in Table 12. These data indicate that NMPK can transform ADP into ATP. Similar experiments can be used to test the ability of other enzymes to perform similar transformations.

TABLE 12

| Reaction | LAR-CoA* | NMPK** | ADP($10^{-5}$ M) | Avg. Light |
|---|---|---|---|---|
| 1 | 100 µl | — | — | 0.58 |
| 2 | 100 µl | 10 µl | — | 0.23 |
| 3 | 100 µl | — | 5 µl | 14.81 |
| 4 | 100 µl | 10 µl | 5 µl | 211.4 |

*Luciferase Assay Reagent formulated without added Coenzyme A or ATP
**Sigma N-4379, Lot #96H0166, dissolved in ATP free water to 3.35 U/ml Example 9
Combination of NMPK and NDPK, dCTP, and AMP One potential method for amplifying an ATP signal requires two enzymes and a phosphate donor. For this system to operate, the first enzyme, E1, must be able to convert AMP to ADP but must be unable to use the phosphate donor. The second enzyme, E2, must be able to effectively use the phosphate donor to transform any ADP formed to ATP. This example demonstrates a method to test the ability of a combination of enzymes to be used in such a combination reaction scheme. The Examples above demonstrate that NDPK can transform ADP to ATP using dCTP as a phosphate donor.

The reactions were assembled as presented in Table 13 and incubated for 30 min at room temperature. Then long of luciferase in 2 µl of 1×CCLR with 1 mg/ml BSA was added and the light output of the reactions was measured using a Turner TD-20e Luminometer. The data is presented in Table 13.

The reaction which could have produced significant ATP if NMPK could transform AMP to ADP using dCTP as a substrate is reaction 4. This reaction produced only minute amounts of ATP as measured by Luciferase mediated light production. Reaction 5 (where NDPK was used to transform ADP to ATP using added dCTP) and reaction 6 (where NMPK was used to transform ADP to ATP) produced much more ATP. Since all enzymes were shown to be active, these data indicate that NMPK essentially cannot use dCTP to transform AMP to ADP. This is the essential requirement for the ATP amplification system described above. In this particular instance E1, NMPK, cannot use the phosphate donor (dCTP) but can utilize AMP and ATP to produce 2 ADP molecules (the reverse of the reaction 6). The second enzyme, E2 (NDPK), can use the phosphate donor (dCTP) to transform the ADP produced by the first enzyme to create 2 ATP from the 2 ADP using 2 dCTP. These ATPs can then re-enter the cycle. This protocol can be used to test combinations of enzymes and phosphate donors for their ability to act as the enzymes in our ATP amplification schemes.

TABLE 13

| Reaction | LAR-CoA | AMP | dCTP | NMPK* | NDPK** | water | Tris-Cl | ADP | Light |
|---|---|---|---|---|---|---|---|---|---|
| 1 | 100 µl | — | — | 10 µl | 1 µl | — | 15 µl | — | 0.0088 |
| 2 | 100 µl | 5 µl | — | — | — | 11 µl | 10 µl | — | 0.126 |
| 3 | 100 µl | — | 10 µl | — | — | 11 µl | 5 µl | — | 0.159 |
| 4 | 100 µl | 5 µl | 10 µl | 10 µl | 1 µl | — | — | — | 10.93 |
| 5 | 100 µl | — | 5 µl | — | 1 µl | 10 µl | — | 10 µl | 4049 |
| 6 | 100 µl | — | — | 10 µl | — | 1 µl | 5 µl | 10 µl | 2309 |
| 7 | 100 µl | — | — | — | — | 11 µl | 5 µl | 10 µl | 115.9 |

*= NMPK concentration at 5 mg/ml of Sigma N4379,
**= NDPK concentration of 10 units/µl Sigma NO379, Nucleoside stocks at: AMP (Sigma A2002, Lot #20H7035), 2 × 10–5M; dCTP (Promega U122A, Lot #6858402), 2 × 10$^{-5}$M, ADP 1 × 10$^{-5}$M (Sigma A2754 Lot #65H7880)

Example 10
Amplification of ATP Using NMPK, NDPK, dCTP and AMP with ATP Spikes

The enzyme combination presented in Example 9 should be capable of greatly increasing the relative ATP concentration through the cyclic amplification reaction scheme presented earlier. This example demonstrates the amplification of different levels of input ATP using these enzymes and nucleosides. The reactions were assembled as presented in Table 14 and incubated at room temperature. When the reactions reached incubation time 0 min, 20 min, 40 min, 60 min, 80 min, 100 min, 120 min, 180 min, and 240 min, 112 µl samples of each reaction were transferred to luminometer tubes and long of luciferase were added. The light output of the reactions was immediately measured using a Turner TD-20e Luminometer. The data is presented in Table 15.

The reactions with ATP added (Reactions 1, 2, and 3) increased in ATP more rapidly than the reactions without added ATP (Reaction 4). The rate of increase of the ATP was dependent upon the amount of ATP first added to the reaction. Thus, this combination of enzymes amplified the input ATP signal and the amount of ATP produced at a particular time was dependent upon the starting amount of ATP added.

In addition, this combination of reactions allows the user to determine if any of the enzymes used are contaminated with unexpected activities that may influence the system. For example, removing the NMPK, dCTP or AMP from the system prevents any ATP accumulation, as expected. However, eliminating the NDPK only has a small influence on the rate of ATP accumulation. These data suggest that the NMPK source used contains a small amount of activity which can take the place of NDPK in this system.

Performing similar experiments should allow a user to determine if other enzymes can be used in such amplifications schemes, as shown in Example 11.

TABLE 14

| Reaction | AMP | dCTP | NMPK | NDPK | ATP |
|---|---|---|---|---|---|
| 1 | 10 µl | 10 µl | 100 µl | 10 µl | 1 pmol |
| 2 | 10 µl | 10 µl | 100 µl | 10 µl | 100 fmol |
| 3 | 10 µl | 10 µl | 100 µl | 10 µl | 10 fmol |
| 4 | 10 µl | 10 µl | 100 µl | 10 µl | — |
| 5 | 10 µl | 10 µl | — | 10 µl | 1 pmol |

TABLE 14-continued

| Reaction | AMP | dCTP | NMPK | NDPK | ATP |
|---|---|---|---|---|---|
| 6 | 10 µl | 10 µl | 100 µl | — | 1 pmol |
| 7 | — | 10 µl | 100 µl | 10 µl | 1 pmol |
| 8 | 10 µl | — | 100 µl | 10 µl | 1 pmol |

TABLE 15

| Reaction | 0 min | 20 min | 40 min | 60 min | 80 min | 100 min | 120 min | 180 min | 240 min |
|---|---|---|---|---|---|---|---|---|---|
| 1 | 95 | 179.5 | 249.9 | 339.5 | 562 | 670.9 | 709.4 | 1157 | 1497 |
| 2 | 20.42 | 37.11 | 54.95 | 85.1 | 122.5 | 164.9 | 206.1 | 409.7 | 746 |
| 3 | 12.3 | 25.09 | 39.37 | 55.79 | 93.8 | 120.5 | 156.1 | 325.7 | 573.7 |
| 4 | 11.8 | 25.54 | 37.45 | 54.64 | 87.8 | 113.1 | 143.8 | 299.1 | 548.7 |
| 5 | 96.4 | 75 | 63.63 | 56.75 | 51.72 | 54.72 | 56.61 | 58.97 | 60.97 |
| 6 | 110 | 183.5 | 247.8 | 285.9 | 426.1 | 503.9 | 624.5 | 958 | 1301 |
| 7 | 91.7 | 99 | 98.6 | 85.2 | 93.2 | 94.2 | 95.4 | 91.5 | 90.4 |
| 8 | 3.521 | 2.755 | 2.31 | 2.058 | 2.092 | 2.173 | 1.682 | 1.088 | 0.73 |

Example 11
Amplification of ATP Using Adenylate Kinase and Pyruvate Kinase

This example demonstrates a second ATP amplification system using a non-nucleoside based phosphate donor. The enzymes used are: adenylate kinase (an enzyme which produced 2 ADP from one ATP and one AMP but which cannot use phosphoenol pyruvate (PEP) as a phosphate donor and Pyruvate Kinase (an enzyme which phosphorylates ADP to form ATP using PEP as a phosphate donor). The reactions were assembled as presented in Table 16. These reactions were incubated at room temperature and 109 µl of the reactions was removed at 0, 30, 60, and 120 min. Luciferase (2 µl, 10 ng in 1×CCLR with 1 mg/ml BSA) was added and the light output of the reaction was immediately measured using a Turner TD-20e Luminometer. The data is presented in Table 17.

After 30 minutes of incubation the reaction containing ATP (reaction 1) increased much more rapidly than the reaction with no ATP added (reaction 2). Thus, the ATP sample was amplified. Also note that in this set of reactions, the ATP content of reactions 1 and 2 reached a final ATP level. This indicates that the reactions had reach an equilibrium value.

Finally, note that the reaction with no added AMP also increased over time. This suggests that one of the components was contaminated with either AMP or ADP.

Further experiments demonstrated that the contaminating nucleoside was present in the pyruvate kinase solution used in this study. The following example demonstrates a method for removing this contaminating nucleoside.

TABLE 16

| Reaction | ATP | AMP | AK | PEP | PK | Tris | Buffer | LAR-CoA |
|---|---|---|---|---|---|---|---|---|
| 1 | 12.5 $\mu$l | 5 $\mu$l | 10 $\mu$l | 5 $\mu$l | 12.5 $\mu$l | — | — | 500 $\mu$l |
| 2 | — | 5 $\mu$l | 10 $\mu$l | 5 $\mu$l | 12.5 $\mu$l | 12.5 $\mu$l | — | 500 $\mu$l |
| 3 | 12.5 $\mu$l | — | 10 $\mu$l | 5 $\mu$l | 12.5 $\mu$l | 5 $\mu$l | — | 500 $\mu$l |
| 4 | 12.5 $\mu$l | 5 $\mu$l | — | 5 $\mu$l | 12.5 $\mu$l | — | 10 $\mu$l | 500 $\mu$l |
| 5 | 12.5 $\mu$l | 5 $\mu$l | 10 $\mu$l | - | 12.5 $\mu$l | — | 5 $\mu$l | 500 $\mu$l |
| 6 | 12.5 $\mu$l | 5 $\mu$l | 10 $\mu$l | 5 $\mu$l | — | — | 12.5 $\mu$l | 500 $\mu$l |

*The concentrations of these components were: ATP, 1 × $10^{-6}$M; AMP, 1 × $10^{-4}$M; Adenylate Kinase (AK) (Sigma M5520, lot #16H9558), 7 U/$\mu$l in 50 mM $KPO_4$, 15 mM $MgCl_2$, pH 7.5 (Buffer A); PEP, (Phosphoenolpyruvate, Sigma P-7002, Lot #46H3777, 100 mM in deionized water; PK (pyruvate kinase, (Sigma P-7286, Lot #45H9504), 0.1 U/$\mu$l in Buffer A), and; Tris Cl, 10 mM Tris Cl, pH 7.5.

TABLE 17

| | Time (Min) | | | |
|---|---|---|---|---|
| Reaction | 0 | 30 | 60 | 120 |
| 1 | 93.6 | 536.4 | 683.8 | 670.4 |
| 2 | 14.98 | 120.6 | 594.8 | 639.3 |
| 3 | 105.5 | 219.4 | 321 | 384.7 |
| 4 | 112.5 | 97.2 | 98.8 | 94.1 |
| 5 | 83.1 | 16.84 | 16.03 | 15.02 |
| 6 | 90.6 | 21.61 | 22.79 | 21.2 |

Example 12
Removal of Interfering Substances in Pyruvate Kinase Using Dialysis

This example demonstrates methods for detecting contaminating nucleosides in enzymes used in the various technologies discussed in the other examples and removing the contaminating material.

Additionally, another amplification scheme is described. This scheme utilizes: Adenylate Kinase (E1); NDPK (E2); AMP; and the ATP analog AMP-CPP as the high energy phosphate donor. If AMP is left out of this reaction, no increase in an initial ATP signal should take place unless one of the other materials is contaminated with AMP (or ADP).

Reactions performed as described in Example 11 suggested that one of the components may have adenosine nucleoside contamination. One of the components suspected of contamination is pyruvate kinase. A sample of this enzyme was dialyzed against 50 mM $KPO_4$, 15 mM $MgCl_2$ pH 7.6 in Spectra Por Dialysis tubing with a molecular weight cut off of 3,500 da. The dialysis was performed twice against 1000×amount of buffer for several hours at 4° C. to remove free adenosine. The reactions were assembled according to Table 18. These data indicate that following dialysis the enzyme solution was slightly more dilute than prior to dialysis. By adding 5.3 $\mu$l of the post dialysis enzyme and 5.0 $\mu$l of the pre-dialysis enzyme, equal amounts of PK were added to the reactions.

500 microliters of LAR-CoA was added to the assembled reactions and the final reactions incubated at room temperature. At 0, 10, 20, and 30 min, 114 $\mu$l of these reactions were added to long of luciferase in 5 $\mu$l of 1×CCLR with 1 mg/ml BSA and the light output of the solutions was immediately measured using a Turner TD-20e Luminometer. The data is presented in Table 19.

Two main observations can be derived from this data. First, the AK, NDPK, AMP, AMP-CPP enzyme-substrate combination can be used to amplify an ATP signal. However, production of ATP from some contamination source allows reactions not given ATP added to achieve a final ATP concentration similar to those given an ATP spike.

The reaction to which no AMP or PK were added (reaction 2) does not increase over time. However, the reactions to which the undialized PK was added and no AMP was added give high light output over time (reaction 5). Addition of dialyzed PK to reactions lacking AMP (reaction 8) demonstrate increased light output over time, but the rate of increase is dramatically reduced from that seen without dialysis.

This Example demonstrates that yet another ATP amplification system can be used to generate higher ATP levels from a starting ATP spike. In addition, this Example shows that these systems can be used to determine if solutions contain contaminating nucleosides and that dialysis can be used to fractionate contaminating nucleosides from enzymes utilized in ATP amplification reactions.

TABLE 18

| Reaction | AMP | ATP | NDPK | AMP-CPP | AK | PK | Pi Buffer | Tris |
|---|---|---|---|---|---|---|---|---|
| 1 | 10 $\mu$l | 10 $\mu$l | 5 $\mu$l | 10 $\mu$l | 10 $\mu$l | — | 5 $\mu$l | — |
| 2 | — | 10 $\mu$l | 5 $\mu$l | 10 $\mu$l | 10 $\mu$l | — | 5 $\mu$l | 10 $\mu$l |
| 3 | 10 $\mu$l | — | 5 $\mu$l | 10 $\mu$l | 10 $\mu$l | — | 5 $\mu$l | 10 $\mu$l |
| 4 | 10 $\mu$l | 10 $\mu$l | 5 $\mu$l | 10 $\mu$l | 10 $\mu$l | 25 $\mu$l Sample 1 | — | — |
| 5 | — | 10 $\mu$l | 5 $\mu$l | 10 $\mu$l | 10 $\mu$l | 25 $\mu$l Sample 1 | — | 10 $\mu$l |
| 6 | 10 $\mu$l | — | 5 $\mu$l | 10 $\mu$l | 10 $\mu$l | 25 $\mu$l Sample 1 | — | 10 $\mu$l |
| 7 | 10 $\mu$l | 10 $\mu$l | 5 $\mu$l | 10 $\mu$l | 10 $\mu$l | 26.5 $\mu$l Sample 2 | — | — |
| 8 | — | 10 $\mu$l | 5 $\mu$l | 10 $\mu$l | 10 $\mu$l | 26.5 $\mu$l Sample 2 | — | 10 $\mu$l |
| 9 | 10 $\mu$l | — | 5 $\mu$l | 10 $\mu$l | 10 $\mu$l | 26.5 $\mu$l Sample 2 | — | 10 $\mu$l |

The compositions of these solutions were: AMP, 1 × $10^{-4}$M; ATP, 2 × $10^{-6}$M; NDPK, 0.1 U/$\mu$l; AMP-CPP, 1 × $10^{-3}$M; AK, 0.75 units/$\mu$l; PK, 5 $\mu$l of pyruvate kinase pre-dialysis (sample 1) or post dialysis (sample 2), Pi buffer (described above); and, Tris, 10 mM Tris - Cl, pH 7.5.

TABLE 19

| Reaction | Time (Min) | | | |
|---|---|---|---|---|
| | 0 | 10 | 20 | 30 |
| 1 | 60.35 | 349.7 | 529 | 563.1 |
| 2 | 54.73 | 50.74 | 49.79 | 52.79 |
| 3 | 51.62 | 59.11 | 279 | 420.7 |
| 4 | 87.4 | 666.6 | 754.2 | 779 |
| 5 | 73.1 | 213.9 | 354.6 | 412.4 |
| 6 | 24.41 | 479.1 | 701.7 | 707.6 |
| 7 | 69.9 | 449.3 | 577.3 | 595.2 |
| 8 | 50.92 | 76.03 | 118.4 | 148.9 |
| 9 | 12.92 | 229.3 | 541.3 | 569.4 |

Example 13
PRPP Synthetase, Reactions with Adenosine

The enzyme 5' phopshorylribose 1' pyrophosphate synthetase (PRPP Synthetase) transfers a pyrophosphate from ATP to D-ribose 5' phosphate. This experiment was performed to determine if this enzyme could be used with AMP and 5' phosphoribose 1' pyrophosphate to generate ATP and D-ribose 5' phosphate.

ATP, AMP and PRPP were diluted in 10 mM Tris, pH 7.3. PRPP Synthetase (Sigma #P0287) was diluted in PRPP Synthetase reaction buffer (see below). 2 µl of ATP, 2 µl of AMP, 2 µl of PRPP, and 2 µl of PRPP Synthetase (or appropriate buffers) were added as indicated in Table 20 to 20 µl of PRPP Synthetase reaction buffer.

The reactions were incubated in the 37° C. water bath for 30 min. The tubes were removed from the water bath and 100 µl of LAR (without CoA) was added. Then, 126 µl was transferred to a luminometer tube. 10 ng of Luciferase was added in 5 µl of 1×CCLR containing 1 mg/ml BSA and light output measured with Turner TD-20e Luminometer. The data presented in Table XXX. This data demonstrates that PRPP Synthetase can transfer pyrophosphate from non-nucleoside substrates to AMP to form ATP.

The nucleoside concentrations in the reaction were: ATP (when added) $1.2 \times 10^5$ M; AMP (when added) $2.9 \times 10^{-5}$ M, and; PRPP (when added) $2.6 \times 10^{-5}$ M. $6 \times 10^{-4}$ units of the enzyme (PRPP Synthetase) was added per reaction. PRPP Synthetase buffer is 50 mM triethanolamine, 50 mM potassium phosphate, pH 7, 0.37 mM EDTA, 10 mM $MgCl_2$, 1 mg/ml BSA.

TABLE 20

| Tube # | AMP | PRPP | PRPP Syn | Light Units | |
|---|---|---|---|---|---|
| 1 | + | + | + | 3440 | 3424 |
| 2 | + | − | + | 0.522 | 0.501 |
| 3 | + | + | − | 6.649 | 4.619 |
| 4 | − | + | + | 7.096 | 7.139 |
| 5 | + | − | − | 1.874 | 0.430 |
| 6 | − | − | − | 5.203 | 4.794 |
| 7 | − | + | + | 96.0 | 0.361 |
| 8 | − | − | − | 462.8 | 0.603 |

Example 14
PRPP Synthetase, Reactions with Deoxyadenosine

Some schemes for the detection of DNA require the conversion of dAMP, generated by nuclease digestion of DNA, to dATP. This example demonstrates that the enzyme PRPP Synthetase can perform the transformation of dAMP to dATP using PRPP as a cosubstrate. In addition, this transformation can be monitored by Luciferase detection at much higher sensitivities if the dATP formed is used to transform ADP to ATP through the action of NDPK added to the reaction.

The reactions were assembled in duplicate as shown in Table 21. The concentrations of the reaction components were: dAMP $2.9 \times 10^{-4}$ M in 10 mM Tris pH 7.3; AMP $2.9 \times 10^{-4}$ M in 10 mM Tris pH 7.3; PRPP $2.6 \times 10^{-4}$ M in 10 mM Tris pH 7.3; PRPP Syn (PRPP Synthetase) (Sigma #P0287) 100×dilution of stock enzyme which is at 0.03 units/µl. The components were added to twenty microliters of PRPP Synthetase Buffer (see Example 13). After incubating for 47 min at 37° C., After incubating, 100 µl of LAR was added to all reactions along with 10 ng of luciferase and the light output of the reactions was immediately measured. The data is presented in Table 22. PRPP was able to utilize dAMP as a substrate (comparing reaction 1 to 2, 3, 4 and 5). However, the amount of light produced by reaction was not very great, probably due to the fact that luciferase uses dATP at a much lower efficiency than ATP as presented earlier.

TABLE 21

| Reaction | dAMP | PRPP | PRPP Syn |
|---|---|---|---|
| 1 | 2 µl | 2 µl | 2 µl |
| 2 | 2 µl | — | 2 µl |
| 3 | 2 µl | 2 µl | — |
| 4 | 2 µl | — | — |
| 5 | — | 2 µl | 2 µl |

TABLE 22

| Reaction | Tube A | Tube B | Avg. |
|---|---|---|---|
| 1 | 18.2 | 22.1 | 20.15 |
| 2 | 1.4 | 1.4 | 1.4 |
| 3 | 4.2 | 3.8 | 4 |
| 4 | 2.1 | 1.8 | 1.95 |
| 5 | 13.1 | 15.8 | 14.45 |

In order to demonstrate the transfer of phosphate from dATP to ADP to form ATP, the reactions presented in Table 23 were assembled in duplicate in twenty microliters of PRPP Synthetase Buffer (for solution compositions, see tables above). They were then incubated at 37° C. for 34 min. The added components had the following formulations: ADP $2.3 \times 10^{-2}$ M in 10 mM Tris pH 7.3; NDPK-1000× dilution of Sigma #N0379 at 10 units/µl (final concentration 0.01 units/µl). The tubes were then incubated for an additional 60 min at 37° C., long of Luciferase were added, and the light output was measured using a Turner TD-20e Luminometer. The data is presented in Table 24. These data indicate that the dATP produced by the PRPP Synthetase reaction can be transferred to ADP by the action of NDPK to produce ATP.

TABLE 23

| Reaction | dAMP | PRPP | PRPP Syn | ADP | NDPK |
|---|---|---|---|---|---|
| 1 | 2 µl | 2 µl | 2 µl | 2 µl | 2 µl |
| 2 | 2 µl | 2 µl | 2 µl | — | — |
| 3 | 2 µl | 2 µl | 2 µl | 2 µl | — |
| 4 | 2 µl | 2 µl | 2 µl | — | 2 µl |
| 5 | — | 2 µl | 2 µl | 2 µl | 2 µl |

TABLE 24

| | Light Units | |
|---|---|---|
| Reaction | Tube A | Tube B |
| 1 | 812.1 | 839.3 |
| 2 | 19.2 | 37.5 |
| 3 | 53.6 | 52.6 |
| 4 | 168.4 | 173.1 |
| 5 | 43.6 | 38.9 |

Example 15
Digestion of PolydA Using Nucleases

One potential method for detecting DNA would be to digest the polymer to deoxynucleoside 5' monophosphate, transform the deoxynucleoside monophosphates to deoxynucleoside triphosphates, form ATP from the deoxynucleoside triphosphates using ADP and NDPK, and then detect the ATP using Luciferase. This example demonstrates the digestion of a deoxyadenosine polymer.

A solution of deoxyadenosine 5' monophosphate was made by adding 990 $\mu$l of water and 10 $\mu$l of 1×TE buffer (10 mM Tris Cl, 1 mM EDTA pH 8.0) to 25 units of polyadenylic acid (Pharmacia 27-786, Lot #5017836021). A reaction was assembled with the following materials: 450 $\mu$l of nanopure water, 50 $\mu$l of 10×S1 Nuclease buffer (Promega Corp. M577A, Lot #6748605) and 10 $\mu$l of the polydeoxyadenylic acid solution above. The absorbance change at 260 nm was monitored on a Beckman DU650 Spectrophotometer. The rate of change in the absorbance of the solution was 0.0020 Abs/min. At this point, 1 $\mu$l of S1 Nuclease (Promega Corp. E576B, Lot #6800810) was added and the absorbance change of the solution redetermined and found to be 0.0156 abs/min. Since small oligonucleosides and mononucleosides display absorbance values higher than a corresponding amount of polynucleoside, this indicates that this enzyme can digest the polymer.

The reaction conditions given below are those used to digest the polydeoxyadenylic acid polymer samples that are used in later examples.

Three reactions were assembled which contained:

Reaction 1: 90 $\mu$l of the polydeoxyadenylic acid solution described above, 10 $\mu$l of 10×S1 nuclease reaction buffer.

Reaction 2: As Reaction 1 above.

Reaction 3: 90 $\mu$l of nanopure water, 10 $\mu$l of S1 nuclease reaction buffer.

At time equals zero minutes of digestion, 10 $\mu$l of each of these was removed and added to 490 $\mu$l of 50 mM Tris Cl pH 8.0. Immediately, 1 $\mu$l of S1 nuclease was added to the remaining reaction mixtures 1 and 3 but not 2, and the mixtures were allowed to incubate at room temperature. Additional 10 $\mu$l samples of the reactions were removed after 20, 50 and 140 min of reaction and diluted into 490 $\mu$l of 50 mM Tris Cl pH 8.0. The data is presented in Table 25. The absorbance of the solution in Reaction #1 increased, again indicating that the polymer in this reaction was digested over time. A second set of reactions was produced as described above. The only difference with these reactions was that 50 units of Sigma Poly(dA)(Sigma P-0887, Lot #67H0226) was dissolved in 1.5 ml of TE buffer and used in the reactions. After the 140 minutes of digestion, these reactions were used as described in Example 16.

TABLE 25

| | Net Absorbance at 260 nm of Samples From Reaction | | |
|---|---|---|---|
| Time | #1 | #2 | #3 |
| 0 | 0 | 0 | 0 |
| 20 | 0.0726 | −0.0088 | −0.0025 |
| 50 | 0.1425 | 0.0291 | −0.0041 |
| 140 | 0.1445 | −0.003 | −0.0044 |

Example 16
Detection of Poly (dA) Using Nucleases and PRPP Synthetase

In this example, the digested polynucleoside described in Example 15 is detected by two different methods. Both methods begin with transformation of the deoxynucleosides to deoxynucleoside triphosphates using PRPP Synthetase and PRPP. In the first method, ADP is converted to ATP using the deoxynucleoside triphosphates formed in the PRPP synthetase reaction and the resulting ATP detected using Luciferase. In the second method, AMP is converted to ATP using the deoxynucleoside triphosphates formed by the PRPP Synthetase reaction, simultaneously amplified and detected using Luciferase.

Table 26 presents the components of the PRPP Synthetase reaction. The concentrations of the components were: PRPP, $2.6 \times 10^{-4}$ M in 10 mM Tris-Cl pH 7.5; PRPP Synthetase, $6 \times 10^{-4}$ Units of Sigma P0287 per 2 $\mu$l in PRPP Synthetase Buffer. For composition of Buffer, refer to PRPP Synthetase Buffer in Example 13. The nucleoside digests containing S1 were diluted in deionized water to yield the amount of polymer listed in the Table in 8 $\mu$l of solution and added to the appropriate reactions. The digest containing no polymer was diluted identically to those with polymer. Eight microliters of this solution contained all the components in the samples containing 720 ng of polymer except the Poly(dA). All the reactions were incubated 32 min in a 37° C. water bath. At this point all the reactions were heated at 95° C. for 5 min to inactivate the PRPP Synthetase and cooled in an ice bath for 5 min.

TABLE 26

| Reaction | Digest | Buffer | PRPP | PRPP Synthetase | poly (dA) | S1 |
|---|---|---|---|---|---|---|
| 1 | 720 ng | 80 $\mu$l | 2 $\mu$l | 2 $\mu$l | — | — |
| 2 | 72 ng | 80 $\mu$l | 2 $\mu$l | 2 $\mu$l | — | — |
| 3 | 7.2 ng | 80 $\mu$l | 2 $\mu$l | 2 $\mu$l | — | — |
| 4 | 0.72 ng | 80 $\mu$l | 2 $\mu$l | 2 $\mu$l | — | — |
| 5 | — | 80 $\mu$l | 2 $\mu$l | 2 $\mu$l | 720 ng | — |
| 6 | — | 80 $\mu$l | 2 $\mu$l | 2 $\mu$l | — | (720 ng |

A. First Detection Method

Twenty microliters of each reaction was added to 100 $\mu$l of LAR minus CoA. Ten nanograms of Luciferase was immediately added and the light production of the reactions was measured. A second 20 $\mu$l sample was added to 100 $\mu$l of LAR minus CoA, followed by addition of ADP (2 $\mu$l of 2 $\mu$g/ml stock) and NDPK (2 $\mu$l of $1 \times 10^{-2}$ U/$\mu$l), and allowed to incubate 20 min at room temperature. After the incubation, 10 ng of luciferase was added to the reactions and the light production of the reactions was measured using a Turner TD-20/20 luminometer at 52.1% sensitivity. The data obtained for these measurements are presented in Table 27.

These data show that direct measurement of the deoxynucleoside triphosphates is possible using luciferase if relatively high amounts of digested DNA are to be detected (see reaction 1 vs. 5 and 6 in the no NDPK column). However, much more sensitive detection is provided when the deoxynucleoside triphosphates are used to convert ADP to ATP using NDPK.

TABLE 27

Light Units

| Reaction | DNA | no NDPK | w/NDPK |
|---|---|---|---|
| 1 | 180 ng | 43 | 711 |
| 2 | 18 ng | 15 | 227 |
| 3 | 1.8 ng | 13 | 77 |
| 4 | 0.18 ng | 11 | 37 |
| 5 | no S1 | 13 | 161 |
| 6 | no poly | 11 | 28 |

B. Second Detection Method

Twenty microliters of the reaction mixtures from the heat inactivated PRPP Synthetase reactions were added to ATP amplification reactions in an attempt to use the initial deoxynucleoside triphosphates to produce of ATP. This would allow easier detection of the dATP produced by the PRPP synthetase reaction.

The reactions were assembled as demonstrated in Table 28. The reactions were mixed and the first aliquot of 109.3 $\mu$l (1/7 of the reaction) was removed immediately after adenylate kinase was added. The aliquot was placed in a luminometer tube, 10 ng luciferase was added, the tube tapped to mix, and then the light output was measured with a Turner TD-20/20 luminometer at 52.1% sensitivity. Subsequent aliquots were removed at 20 minute intervals and measured immediately. The reactions were incubated at room temperature. The data obtained is presented in Table 29.

These results show that it is possible to amplify the dATP produced from digested DNA after conversion to nucleoside triphosphates. Note that the light output obtained by this method is greater than the light output of the non-amplified PRPP Synthetase method.

TABLE 29

| | 0 minutes* | 20 minutes* | 40 minutes* |
|---|---|---|---|
| 1 | 11.56 | 187.30 | 5860.0 |
| 2 | 1.89 | 25.26 | 1598.0 |
| 3 | 2.09 | 12.52 | 671.3 |
| 4 | 1.34 | 20.21 | 1638.0 |
| 5 | 1.56 | 17.04 | 1009.0 |
| 6 | 1.11 | 9.44 | 691.1 |
| 7 | 27.21 | 315.30 | 7426.0 |
| 8 | 8.84 | 186.20 | 7177.0 |
| 9 | 1.52 | 9.76 | 295.6 |
| 10 | 1.14 | 5.18 | 184.1 |
| 11 | 0.72 | 4.10 | 169.7 |

*Light output in Relative Light Units

Example 17
Digestion of PhiX 174 HinF1 Fragments

Polynucleoside encountered in nature is often double stranded. The DNA fragments generated by digestion of Phi X 174 DNA using endonuclease HinF I are double stranded DNA fragments of various sizes. In order to test whether double stranded DNA could be detected, the Phi X 174 was directed used as a test substrate or digested with nucleases to produce nucleosides which could be converted to nucleoside triphosphates as in previous Examples.

The following conditions were used to digest DNA fragments from bacteriophage Phi X 174. These materials were placed in three 1.5 ml polypropylene tubes: 50 $\mu$l of PhiX174 Hin FI fragments (Promega G175A, Lot #773603); 40 $\mu$l of 5 mM Mg SO$_4$; 5 $\mu$l of Exo III buffer (10×) (Promega E577B, 4853216), and 5 $\mu$l of Nanopure water. Fifty microliters of TE buffer and 40 $\mu$l of 5 mM MgSO$_4$; 5 $\mu$l of ExoIII buffer (10×) and 5 $\mu$l of Nanopure water were added to one sample. Two of the samples containing Phi X 174 DNA were further treated with 2 $\mu$l of Exo III (Promega M181A, 5512708) and the tubes placed in a 37° C. water bath for 60 min. ExoIII was also deleted to the sample without DNA and the sample incubated at 37° C. for 60 min.

At this time, 800 $\mu$l of nanopure water and 100 $\mu$l of S1 Nuclease Buffer (10×) (Promega M577A, Lot #6748605)

TABLE 28

(Reaction Components**)

| Reaction | DNA | LAR-CoA | AMP | PEP | AK | PK | Tris | PRPP Buffer |
|---|---|---|---|---|---|---|---|---|
| 1 | poly (dA) 180 ng, 20 $\mu$l* | + | + | + | + | + | — | – |
| 2 | poly (dA) 18 ng, 20 $\mu$l* | + | + | + | + | + | – | – |
| 3 | poly (dA) 1.8 ng, 20 $\mu$l* | + | + | + | + | + | – | – |
| 4 | poly (dA) | + | + | + | + | + | – | – |
| 5 | poly (dA) no S1 | + | + | + | + | + | – | – |
| 6 | S1 nuclease, no | + | + | + | + | + | – | – |
| 7 | ATP 14 $\mu$l 2 mM | + | + | + | + | + | – | 6 $\mu$l |
| 8 | dATP 14 $\mu$l 2 mM | + | + | + | + | + | – | 6 $\mu$l |
| 9 | dATP 14 $\mu$l 200 nM | + | + | + | + | + | – | 6 $\mu$l |
| 10 | dATP 14 $\mu$l 20 nM | + | + | + | + | + | – | 6 $\mu$l |
| 11 | none | + | + | + | + | + | 14 $\mu$l | 6 $\mu$l |

*These reactions used 20 $\mu$l of the heat-inactivated PRPP Synthetase reactions from the first part of this example.
**The components were: ATP (Sigma A9187) in 10 mM Tris pH 7.5, dATP (Sigma D6500) in 10 mM Tris pH 7.5, AMP 7 $\mu$l of 2 × 10$^{-4}$M in 10 mM Tris pH 7.5, LAR-CoA (LAR without CoA) 700 $\mu$l per reaction tube, PEP (phosphoenol pyruvate-ammonium salt) (synthesized) 7 $\mu$l of 100 mM, AK (adenylate kinase/myokinase) (Sigma M5520) 14 $\mu$l of 0.75 units/$\mu$l in Buffer A, PK (pyruvate kinase) (Sigma P7286, dialyzed 48 hours) 17.5 $\mu$l of 0.13 units/$\mu$l, Tris 10 mM pH 7.5, PRPP Synthetase Buffer-see example 13.

were added to all samples. Three microliters of S1 nuclease (Promega E576B, Lot #789881) were then added to all samples. All samples were incubated at 37° C. for 30 min. Two hundred microliters from each of the three tubes containing DNA were diluted with 300 µl of 1×TE Buffer and the absorbance read at 260 nm using a Beckman DU 650 spectrophotometer. The readings recorded were: tube one (no nuclease addition), 0.3073; tube two (treatment with Exo III), 0.5495; tube three (treatment with Exo III and S1), 0.5190. The increased absorbance values of the tubes treated with nuclease indicates that the polymer was digested. These digests were subsequently used in other studies (see Example 18).

Example 18
Detection of PhiX 174 Hin F1 Fragments Using Nucleases, PRPP Synthetase, NDPK This example demonstrates the detection of DNA by digestion of the polymer to nucleoside monophosphates using nucleases, transformation of the nucleoside monophosphates to nucleoside triphosphates using PRPP Synthetase and PRPP along with transformation of ADP to ATP using the nucleoside triphosphates generated by the action of PRPP Synthetase, and detection of the ATP using Luciferase. A sample of deoxynucleoside (Poly (dA)) was prepared as described in example 17. Different amounts of deoxynucleoside were used in the reactions as presented in Table 30.

The following additions were made to each reaction: 2 µl of PRPP, 2 µl of PRPP Synthetase, and 20 µl PRPP Synthetase buffer. The reactions proceeded at 37° C. for 28 minutes at which time the reactions were transferred to 100 µl containing 2 µl of ADP and 2 µl of NDPK. This second reaction was allowed to proceed at room temperature for 20 min. The amount of ATP produced was measured by the addition of 10 ng of Luciferase followed by measuring light output with a luminometer. The data is presented in Table 30.

These data show that this combination of enzymes allows detection of DNA.

TABLE 30

| Reaction | Nucleoside | Amount in Rxn | Light Units |
|---|---|---|---|
| 1 | dAMP | 200 ng, 600 pmoles | 1018 |
| 2 | dAMP | 20 ng, 60 pmoles | 636 |
| 3 | dAMP | 2 ng, 6 pmoles | 178 |
| 4 | dAMP | 200 pg, 600 fmoles | 83 |
| 5 | none | 0 ng | 69 |
| 6 | Phi X174 only | 100 ng (= 300 pmoles dNMP; approx. 75 pmoles dAMP) | 46 |
| 7 | Phi X174 + ExoIII | 100 ng | 472 |
| 8 | Phi X174 + Exo + S1 | 100 ng | 448 |
| 9 | No DNA + Exo + S1 | 0 ng | 55 |

Example 19
Detection of PhiX 174 Hin F1 Fragments Using Reverse Transcriptase and NDPK The following example demonstrates the detection of DNA fragments having nucleoside overhangs on their ends using reverse transcriptase. The reactions were assembled as demonstrated in Table 31.

The components were: Buffer, 5×MMLV-RT Buffer, (Promega Part #M531A, Lot #7090101); DNA, PhiX 174 Hin F1 Fragments (Promega Part #G175A, Lot #7733602); NaPP$_i$, 10 mM Sodium Pyrophosphate (Promega Part #C113A, Lot #6675705); ADP, 1 µM ADP (Sigma A-5285, Lot #56H7815); NDPK, nucleoside diphosphate kinase, (Sigma N-0379, Lot #127F81802) 1 U/µl in 25 mM sodium citrate; MMLV-RT (Promega M170A, Lot #6980019, 1 U/µl), incubated for 30 min at 37° C., then 2 µl of the reactions was added to 100 µl of L/L (Promega FF2021, Enliten Luciferase/Luciferin Reagant). The light production by the reactions was immediately measured with a Turner TD-20e Luminometer The data is presented in Table 31.

These data show that MMLV-RT can be used to pyrophosphorylate DNA and that the resulting nucleosides can be used to transform ADP to ATP and the ATP formed detected using Luciferase. Other enzymes can be tested for their ability to perform this reaction in a similar fashion.

TABLE 31

| Rx | Buffer | DNA | NaPPi | ADP | NDPK | water | MMLV-RT | Light |
|---|---|---|---|---|---|---|---|---|
| 1 | 4 µl | 1 µl of 100 ng/µl | 1 µl | 2 µl | 1 µl | 10 µl | 1 µl | 165. |
| 2 | 4 µl | 1 µl of 20 ng/µl | 1 µl | 2 µl | 1 µl | 10 µl | 1 µl | 155. |
| 3 | 4 µl | 1 µl of 4 ng/µl | 1 µl | 2 µl | 1 µl | 10 µl | 1 µl | 58.9 |
| 4 | 4 µl | 1 µl of 800 pg/µl | 1 µl | 2 µl | 1 µl | 10 µl | 1 µl | 18.0 |
| 5 | 4 µl | 1 µl of 160 ng/µl | 1 µl | 2 µl | 1 µl | 10 µl | 1 µl | 4.54 |
| 6 | 4 µl | 1 µl of 32 ng/µl | 1 µl | 2 µl | 1 µl | 10 µl | 1 µl | 1.70 |
| 7 | 4 µl | — | 1 µl | 2 µl | 1 µl | 11 µl | 1 µl | 0.95 |
| 8 | 4 µl | 1 µl of | | 1 µl | 2 µl | 1 µl | 11 µl | 0.62 |

Example 20
Limit of DNA Fragment Detection Using Reverse Transcriptase, NDPK, and Luciferase As shown in Example 18, DNA can be detected using luciferase when the DNA is fragmented and pyrophosphorylated using a reverse transcriptase to produce dNTPs and the terminal phosphate is transferred from the dNTPs to ADPs to form ATP. This Example demonstrates that the light units produced in reaction containing very low levels of DNA are statistically significant compared to values for the appropriate control reactions. As with Example 2, the limit of detection is statistically determined using Student's t-Test. The reactions presented in Table 32 were assembled in duplicate. The components were: Buffer 5×MMLV-RT Buffer (Promega M531A); DNA, PhiX 174 Hin F1 fragments diluted in TE (Promega G175A); TE, Tris EDTA (Promega AA641); NaPPi, 40 mM Sodium Pyrophosphate (Promega C113A); ADP, ADP 2 uM in Tris 10 mM pH 7.3 (Sigma A5285); NDPK, 1 unit/µl in water (Sigma N0379); water, nanopure water; MMLV-RT, MMLV reverse transcriptase 200 units/µl (Promega M170A).

All reagents except DNA and MMLV-RT were added to a 1.5 ml polypropylene tube and mixed. Then duplicate 16.5 µl aliquots were transferred to new polypropylene tubes.

One microliter of MMLV-RT was added to each tube, followed by 2.5 μl of DNA at varying concentrations or 2.5 μl of TE. The reactions were incubated at 37° C. for 10 min, then 2 μl of the 20 μl reaction was added to 100 μl of L/L reagant (which includes luciferase, Promega F202A and F180A, mixed) in a luminometer tube. The tubes were tapped to mix, and then light output levels were immediately measured using a Turner TD-20e luminometer at 52.1% sensitivity (this sensitivity is comparable to the Turner TD-20/20 readings). The data is presented in Table 33.

The light output for each DNA concentration (6 readings each) was compared to the light output of the background control (no DNA), and a p-value determined for each comparison. The results of the analysis are presented in the following Table 34. As in Experiment 2, the p-values were less than 0.05 for each sample tested. Therefore, less than 10 pg of DNA can be reliably detected.

scriptase. A reaction master mix was made containing: 80 μl of 5×MMLV-RT Buffer (Promega Part #M531A, Lot #7090101); 10 μl of 40 mM Sodium Pyrophosphate (Promega Part #C113A, Lot #6675705); 10 μl of 1 μM ADP (Sigma A-5285, Lot #56H7815); 20 μl of NDPK (Sigma N-0379, Lot #127F81802 1 U/μl); and 210 μl of deionized water.

DNA samples consisted of ladders of DNA fragments in multiples of 25 bp (Promega G451, Lot #84791) and 50 bp (Promega G452, Lot #84796) in 1×TE buffer. These materials were diluted into 1×TE buffer to produce a series of solutions at different DNA concentrations. The reactions were assembled as demonstrated in Table 35. The composition of these components was: MM, Master Mix (described above), and 200 U/μl MMLV-RT (Promega Part #M531A).

These reactions were incubated for 30 min at 37° C. After incubation, 2 μl of the solution was added to 100 μl of L/L

TABLE 32

| Reaction | Buffer | DNA | TE | NaPPi | ADP | NDP | water | MMLV-RT |
|---|---|---|---|---|---|---|---|---|
| 1 | 4 μl | — | 2.5 μl | 0.5 μl | 1 μl | 1 μl | 10 μl | 1 μl |
| 2 | 4 μl | 2.5 μl of 40 pg/μl | — | 0.5 μl | 1 μl | 1 μl | 10 μl | 1 μl |
| 3 | 4 μl | 2.5 μl of 100 pg/μl | — | 0.5 μl | 1 μl | 1 μl | 10 μl | 1 μl |
| 4 | 4 μl | 2.5 μl of 200 pg/μl | — | 0.5 μl | 1 μl | 1 μl | 10 μl | 1 μl |

TABLE 33

| Reaction | Amount of DNA | Light Units |
|---|---|---|
| 1 | no DNA tube 1A | 1.166 |
| 2 | no DNA tube 1A | 1.189 |
| 3 | no DNA tube 1A | 1.190 |
| 4 | no DNA tube 1B | 1.071 |
| 5 | no DNA tube 1B | 1.124 |
| 6 | no DNA tube 1B | 1.159 |
| 7 | 10 pg DNA tube 2A | 1.355 |
| 8 | 10 pg DNA tube 2A | 1.498 |
| 9 | 10 pg DNA tube 2A | 1.464 |
| 10 | 10 pg DNA tube 2B | 1.485 |
| 11 | 10 pg DNA tube 2B | 1.519 |
| 12 | 10 pg DNA tube 2B | 1.189 |
| 13 | 25 pg DNA tube 3A | 2.360 |
| 14 | 25 pg DNA tube 3A | 2.159 |
| 15 | 25 pg DNA tube 3A | 2.344 |
| 16 | 25 pg DNA tube 3B | 2.126 |
| 17 | 25 pg DNA tube 3B | 2.087 |
| 18 | 25 pg DNA tube 3B | 2.148 |
| 19 | 50 pg DNA tube 4A | 4.501 |
| 20 | 50 pg DNA tube 4A | 4.920 |
| 21 | 50 pg DNA tube 4A | 4.751 |
| 22 | 50 pg DNA tube 4B | 4.721 |
| 23 | 50 pg DNA tube 4B | 4.809 |
| 24 | 50 pg DNA tube 4B | 4.929 |

TABLE 34

Student's t-Test for DNA detection

|  | p-value |
|---|---|
| 10 pg | 0.002377925 |
| 25 pg | 3.9211E-07 |
| 50 pg | 4.2734E-09 |

Example 21

Detection of Blunt End DNA Fragments Using Reverse Transcriptase and NDPK

The following example demonstrates the detection of DNA fragments having blunt ends using reverse tranreagent and the light production of the reaction was measured using a Turner TD-20e Luminometer. The data is presented in Table 35. These data demonstrate that sensitive DNA detection of blunt ended fragments can be achieved through pyrophosphorolysis of the DNA followed by conversion of ADP to ATP.

TABLE 35

| Rx | MM | DNA | MMLV-RT | Light |
|---|---|---|---|---|
| 1 | 18 μl | 100 ng 25 bp ladder | 1 μl | 142.5 |
| 2 | 18 μl | 20 ng 25 bp ladder | 1 μl | 66.28 |
| 3 | 18 μl | 4 ng 25 bp ladder | 1 μl | 20.33 |
| 4 | 18 μl | 800 pg 25 bp ladder | 1 μl | 5.216 |
| 5 | 18 μl | 160 pg 25 bp ladder | 1 μl | 1.606 |
| 6 | 18 μl | 32 pg 25 bp ladder | 1 μl | 0.902 |
| 7 | 18 μl | — | 1 μl | 0.717 |
| 8 | 18 μl | 100 ng 25 bp ladder | — | 0.571 |
| 9 | 18 μl | 100 ng 50 bp ladder | 1 μl | 149.2 |
| 10 | 18 μl | 20 ng 50 bp ladder | 1 μl | 84.43 |
| 11 | 18 μl | 4 ng 50 bp ladder | 1 μl | 27.56 |
| 12 | 18 μl | 800 pg 50 bp ladder | 1 μl | 6.694 |
| 13 | 18 μl | 160 pg 50 bp ladder | 1 μl | 2.829 |
| 14 | 18 μl | 32 pg 50 bp ladder | 1 μl | 1.323 |
| 15 | 18 μl | — | 1 μl | 0.951 |
| 16 | 18 μl | 100 ng 50 bp ladder | — | 0.751 |

Example 22

Detection of PolyA RNA Using Poly A Polymerase

This example demonstrates the detection Poly A mRNA by the pyrophosphorylation of the poly A segment. The reactions were assembled as demonstrated in Table 36. The compositions of the reaction materials was: 10×Buffer-0.5M Tris-HCl, pH 7.5, 0.1M $MgCl_2$, 0.5M NaCl; Globin mRNA GibcoBRL cat#18103-028 (dissolved in $H_2O$); $NaPP_i$, 20 mM sodium pyrophosphate (Promega C113A, in deionized water); Poly A Polymerase, (Sigma P4058, 1 U/μl) These reactions were incubated at 37° C. for 30 min, then 2 μl of the reaction was added to 100 μl of L/L Reagent and the light output of the reaction immediately measured using a Turner TD-20e Luminometer. The data is presented in Table 37. These data demonstrate that Poly A Polymerase is capable of pyrophosphorylating the RNA and that the resulting nucleoside triphosphates can be detected using luciferase, even if only very low levels of RNA are present.

10 mM ADP (Sigma A-5285 Lot #56H7815); NDKP, nucleoside diphosphate kinase, 1 U/μl, (Sigma N-0379 Lot #127F81802); MMLV-RT, (Promega Part #M531A, Lot #7090101) 200 U/μl; and 200 U/μl Superscript II GibcoBRL cat# 18064-014)

These reactions were incubated at 37° C. for 30 min and 2 μl of the reactions was added to 100 μl of L/L reagent. The light production of the reactions was immediately measured using a Turner TD-20e Luminometer. The data is presented in Table 39.

TABLE 38

| Rx | Buffer | mRNA | Poly (dT) | NaPPi | ADP | NDPK | MMLV-RT | Superscript | water |
|----|--------|------|-----------|-------|-----|------|---------|-------------|-------|
| 1 | 4 μl | 1 μl of 50 ng/μl | 1 μl | 1 μl | 2 μl | 1 μl | 1 μl | — | 9 μl |
| 2 | 4 μl | 1 μl of 10 ng/μl | 1 μl | 1 μl | 2 μl | 1 μl | 1 μl | — | 9 μl |
| 3 | 4 μl | 1 μl of 2 ng/μl | 1 μl | 1 μl | 2 μl | 1 μl | 1 μl | — | 9 μl |
| 4 | 4 μl | 1 μl of 400 pg/μl | 1 μl | 1 μl | 2 μl | 1 μl | 1 μl | — | 9 μl |
| 5 | 4 μl | 1 μl of 80 pg/μl | 1 μl | 1 μl | 2 μl | 1 μl | 1 μl | — | 9 μl |
| 6 | 4 μl | — | 1 μl | 1 μl | 2 μl | 1 μl | 1 μl | — | 9 μl |
| 7 | 4 μl | 1 μl of 50 ng/μl | 1 μl | 1 μl | 2 μl | 1 μl | — | 1 μl | 9 μl |
| 8 | 4 μl | 1 μl of 10 ng/μl | 1 μl | 1 μl | 2 μl | 1 μl | — | 1 μl | 9 μl |
| 9 | 4 μl | 1 μl of 2 ng/μl | 1 μl | 1 μl | 2 μl | 1 μl | — | 1 μl | 9 μl |
| 10 | 4 μl | 1 μl of 400 pg/μl | 1 μl | 1 μl | 2 μl | 1 μl | — | 1 μl | 9 μl |
| 11 | 4 μl | 1 μl of 80 pg/μl | 1 μl | 1 μl | 2 μl | 1 μl | — | 1 μl | 9 μl |
| 12 | 4 μl | — | 1 μl | 1 μl | 2 μl | 1 μl | — | 1 μl | 9 μl |

TABLE 36

| Reaction | 10X | Globin | NaPPi | Poly A | Water |
|----------|-----|--------|-------|--------|-------|
| 1 | 2 μl | 1 μl of 50 ng/μl | 1 μl | 1 μl | 15 μl |
| 2 | 2 μl | 1 μl of 10 ng/μl | 1 μl | 1 μl | 15 μl |
| 3 | 2 μl | 1 μl of 2 ng/μl | 1 μl | 1 μl | 15 μl |
| 4 | 2 μl | 1 μl of 400 pg/μl | 1 μl | 1 μl | 15 μl |
| 5 | 2 μl | 1 μl of 80 pg/μl | 1 μl | 1 μl | 15 μl |
| 6 | 2 μl | 1 μl of 16 pg/μl | 1 μl | 1 μl | 15 μl |
| 7 | 2 μl | — | 1 μl | 1 μl | 15 μl |

TABLE 37

| Reaction | Light | RNA Present in L/L |
|----------|-------|--------------------|
| 1 | 772.2 | 5000 pg |
| 2 | 172.3 | 1000 pg |
| 3 | 33.53 | 200 pg |
| 4 | 7.727 | 40 pg |
| 5 | 1.85 | 8 pg |
| 6 | 0.743 | 1.6 pg |
| 7 | 0.594 | — |

TABLE 39

| Rx | mRNA | Light Units |
|----|------|-------------|
| 1 | 5 ng | 647.2 |
| 2 | 1 ng | 425.4 |
| 3 | 0.2 ng | 113.9 |
| 4 | 40 pg | 43.56 |
| 5 | 8 pg | 23.66 |
| 6 | — | 21.52 |
| 7 | 5 ng | 648.5 |
| 8 | 1 ng | 500.4 |
| 9 | 0.2 ng | 144.2 |
| 10 | 40 pg | 45.85 |
| 11 | 8 pg | 28.17 |
| 12 | — | 19.71 |

Example 23

Detection of Poly A RNA using Reverse Transcriptase and NDPK

This example demonstrates another method for the detection of mRNA, particularly polyA mRNA. In this method, a DNA segment is hybridized to the mRNA and the probe is pyrophosphorylated using a reverse transcriptase and pyrophosphate. As the pyrophosphorylation occurs, the deoxynucleoside triphosphates are used to convert ADP to ATP using the enzyme NDPK. The ATP of the final solution is then measured using luciferase.

The reactions were assembled as presented in Table 38. The reaction components were: Buffer, 5×MMLV-RT Buffer (Promega Part #M531A, Lot #7090101); mRNA, Globin mRNA (GibcoBRL cat# 18103-028 dissolved in H₂O); Poly (dT), 0.2 μM oligo dT(50), NaPPi, 20 mM Sodium Pyrophosphate, (Promega C113A in deionized water); ADP,

Example 24

Detection of RNA Using Nucleases, PRPP Synthetase

This example demonstrates the detection of RNA by digestion of RNA by nucleases, transformation of the AMP produced to ATP by PRPP Synthetase, and detection of the ATP produced using Luciferase. Three reactions were assembled. These were: Digest 1 (250 ng Globin mRNA and S1 in a 10 μl reaction); Digest 2 (same as Digest 1, however no S1 nuclease was added); Digest 3 (same as Digest 1, but without Globin mRNA). After these digests had incubated 30 min at 37° C., they were used to compose the reactions presented in Table 40. [For the concentrations of these solutions, see descriptions under reaction composition table in Example 16.]

The reactions were incubated for 30 min at 37° C., 100 μl of LAR-CoA and 10 ng of Luciferase were added to each tube, and the light output of the reactions were measured using a Turner TD-20e Luminometer. The data is presented in Table 40. These data show that this combination of enzymes can be used to detect relatively low levels of RNA.

TABLE 40

| Reaction | AMP | Digest # and µl | Polymer Added | PRPP Synthetase Buffer | PRPP Synt | Light Units |
|---|---|---|---|---|---|---|
| 1 | 2 µl of 2.9e-4M (200 ng) | — | — | 20 µl | 2 µl | 3869 |
| 2 | 2 µl of 2.9e-5M (20 ng) | — | — | 20 µl | 2 µl | 1287 |
| 3 | 2 µl of 2.9e-6M (2 ng) | — | — | 20 µl | 2 µl | 192.9 |
| 4 | 2 µl of 2.9e-7M (200 pg) | — | — | 20 µl | 2 µl | 118.6 |
| 5 | — | 1, 0.2 µl | 5 ng | 20 µl | 2 µl | 48.4 |
| 6 | — | 1, 0.02 µl | 0.5 ng | 20 µl | 2 µl | 14.8 |
| 7 | — | 2, 0.2 µl | 5 ng | 20 µl | 2 µl | 10.9 |
| 8 | — | 2, 0.02 µl | 0.5 ng | 20 µl | 2 µl | 10.6 |
| 9 | — | 3, 0.2 µl | — | 20 µl | 2 µl | 10.3 |
| 10 | — | 3, 0.02 µl | — | 20 µl | 2 µl | 11 |

Example 25

Improved Detection of Cells Through the Addition of Materials that Allow ATP to be Produced from the Enzymes in the Cells One common way to detect the presence of cells is to assay the ATP content of materials which may contain cells. However, such detection methods are limited by the very small concentration of ATP that is present in samples which may contain very few cells. Several types of enzymatic activities are required in every living cell. These activities are involved in the transformation of nucleosides into nucleoside triphosphates for use in cellular metabolism. In particular, the activities known as adenylate kinase and nucleoside diphosphokinase are widely found in cells. Since these enzymes are expected to exist in all cell lysates, addition of AMP and dCTP should result in the formation of ATP in cell lysates through the reactions:

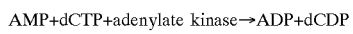

AMP+dCTP+adenylate kinase→ADP+dCDP

ADP+dCTP+NDPK→ATP+dCDP

If, however, the enzymes which remove ATP from such extracts are active enough to remove the ATP as it is formed, no build-up of ATP will result.

This example demonstrates that ATP can be detected in cell lysate samples to which AMP and dCTP are added. The nucleoside transformations such as those presented above probably increase ATP concentration. Therefore, lower amounts of cells and cellular materials can be detected by taking advantage of the transformation activity of these enzymes to produce ATP from AMP thereby detecting ATP directly.

A sample of *E. coli* JM109 was grown in Luria broth for 2 hours. The cells were harvested by centrifugation at 7240 g for 10 min and then resuspended in 1×TBS. The cells were spun down again the same way and resuspended in 1×TBS. A sample of the resuspended cells was removed, diluted into sterile Luria broth and plated onto Luria Agar plates to determine the number of cells per microliter of resuspended cell culture. The cell culture was then lysed by sonication and the lysate was used in the reactions presented in Table 41. After an incubation of 40 min at room temperature, 10 ng of luciferase was added to the reactions and the light output of the reactions was immediately measured using a Turner TD 20-e luminometer. The data is presented in Table 41.

TABLE 41

| Reaction | Lysate | AMP (0.1 mM) | dCTP (1 mM) | Buffer* | Light |
|---|---|---|---|---|---|
| 1 | 10 µl** | — | 2 µl | 100 µl | 142 |
| 2 | 10 µl** | 2 µl | — | 100 µl | 69 |
| 3 | 10 µl** | — | — | 100 µl | 67 |
| 4 | — | 2 µl | 2 µl | 100 µl | 4 |
| 5 | 10 µl** | 2 µl | 2 µl | 100 µl | 175 |
| 6 | 1 µl** | 2 µl | 2 µl | 100 µl | 18.85 |
| 7 | 0.1 µl | 2 µl | 2 µl | 100 µl | 4.6 |
| 8 | 0.01 µl | 2 µl | 2 µl | 100 µl | 3.5 |

*buffer = 100 µl LAR
**Lysate made from resuspended cells at a concentration of 1.8 × 10⁵ cells/µl. Dilutions of this lysate were made in 1 X TBS and 10 µl added to 5, 6, 7, and 8, the amount of initial lysate equivalent to that added is above.

This data shows that addition of dCTP (reaction 1) allows more light to be measured from a cell sample than can be measured if no addition was made to the lysate (reaction 3) or if AMP alone was added to the lysate (reaction 2). However, even more light can be found if both AMP and dCTP is added to the lysate (reaction 5). Dilution of the lysate results in a reduction of the light produced by reactions given AMP and dCTP (reactions 6 and 7). However, the amount of light found is still above the amount expected to present by simple dilution of the lysate. These data then, show that improved cell detection can be demonstrated if additions can be made to the lysate which should result in an increased ATP level in the sample.

Example 26

Optimization of the Concentrations of Nucleotides Added to Form Additional ATP in Cell Lysates Example 25 demonstrates that additional ATP can be detected in cell lysates if materials are added to the lysate. This example demonstrates that the concentration of the material added can be adjusted to produce a substantially higher level of ATP than is originally present in the lysates. A cell lysate produced from a known amount of cells was produced as in Example 23. This new lysate was used in the reactions presented in Table 42. The reactions were incubated for 40 min at room temperature. After incubation, 10 ng of luciferase was added to the reactions and the light output of the reactions was immediately read using a Turner TD-20e luminometer. The data is presented in Table 42.

These data indicate that the concentration of both nucleotides can be co-optimized to obtain light values far superior to those seen in either the lysate without additions or with non-optimal additions.

TABLE 42

| Reaction | Stock AMP conc. | Stock dCTP conc. | Lysate | LAR-CoA | Light |
|---|---|---|---|---|---|
| 1 | — | 100 mM | 10 μl* | 100 μl | 144.8 |
| 2 | 80 mM | — | 10 μl* | 100 μl | 1.515 |
| 3 | — | — | 10 μl* | 100 μl | 38.4 |
| 4 | 80 mM | 100 nM | — | 100 μl | 1.743 |
| 5 | 0.1 mM | 1 nM | 10 μl* | 100 μl | 139.4 |
| 6 | 1 mM | 1 mM | 10 μl* | 100 μl | 247.3 |
| 7 | 10 mM | 1 mM | 10 μl* | 100 μl | 569.2 |
| 8 | 80 mM | 1 mM | 10 μl* | 100 μl | 336.7 |
| 9 | 80 mM | 1 mM | 10 μl* | 100 μl | 273.9 |
| 10 | 1 mM | 1 mM | 10 μl* | 100 μl | 283.3 |
| 11 | 1 mM | 10 mM | 10 μl* | 100 μl | 239.6 |
| 12 | 1 mM | 100 mM | 10 μl* | 100 μl | 358.8 |
| 13 | 10 mM | 1 mM | 10 μl* | 100 μl | 666.7 |
| 14 | 10 mM | 10 mM | 10 μl* | 100 μl | 1236 |
| 15 | 10 mM | 100 mM | 10 μl* | 100 μl | 2320 |
| 16 | 80 mM | 1 mM | 10 μl* | 100 μl | 339.8 |
| 17 | 80 mM | 10 mM | 10 μl* | 100 μl | 761.9 |
| 18 | 80 mM | 100 mM | 10 μl* | 100 μl | 1970 |

*lysate was made from resuspended cells at a concentration of $3 \times 10^4$ cells/ul
**2 μl of stock used

Example 27
Time Course of ATP Increase in Lysates Following Addition of Enzyme Substrates The examples above indicate cell detection sensitivity increased by addition of dCTP and/or AMP followed by an incubation period prior to ATP detection using luciferase This example demonstrates that detection reaction may be temporally optimized as well.

The cell lysate was made as in Example 25 and was frozen. This lysate was thawed and used to compose the reactions presented in Table 43. Samples were removed from reaction 5 at 1, 5, 15, 30, 60, 90, 120, 150, and 180 min and at 5 min for the other reactions. These samples were added to 10 ng of luciferase and the light output of the reaction was measured immediately using a Turner TD-20e luminometer. The results from the samples taken at 5 min are presented in Table 43. The results from the samples of reaction 5 taken over time are presented in Table 44.

Note that the light output for the reaction rises dramatically over time and reaches final values far above those reported in the previous example. These data indicate that the most sensitive detection of cells will require optimization of the reaction time used for detection in addition to optimization of the added materials.

TABLE 43

| Reaction | Lysate | AMP | dCTP | Light |
|---|---|---|---|---|
| 1 | 10 μl | — | 100 mM | 329 |
| 2 | 10 μl | 10 mM | — | 80.4 |
| 3 | 10 μl | — | — | 241.8 |
| 4 | — | 10 mM | 100 mM | 1.129 |
| 5 | 10 μl | 10 mM | 100 mM | 347.5 |

TABLE 44

| Time | Light |
|---|---|
| 1 | 136.5 |
| 5 | 347.5 |
| 15 | 1325 |
| 30 | 6379 |

TABLE 44-continued

| Time | Light |
|---|---|
| 60 | 21078 |
| 90 | 33204 |
| 120 | 41470 |
| 150 | 43844 |
| 180 | 36579 |

Example 28

Determination of the Effect of Increasing the Number of DNA Ends on Detection of DNA Through Pyrophosphorylation Reverse transcriptases and DNA polymerases usually bind to DNA segments which can be used as substrates in polymerization reactions. Plasmid DNAs have no DNA ends since they are a covalently closed circular molecule. In general, such a molecule would not be expected to undergo pyrophosphorylation unless the DNA is first modified to transform it into a substrate for the reverse transcriptase or polymerase. In this example, an experiment is described that confirms that plasmid DNA is not as good a substrate for pyrophosphorylation as digested fragments. In addition, using an enzyme to cleave the DNA which generates more new DNA ends than one that generates fewer ends may improve the detection of the DNA.

The reactions were assembled as presented in Table 45. The components were: Plasmid, pGEM 3ZF(+) (1 mg/ml, Promega corporation, Part #P227A); Buffer, 10×Buffer B (Promega Corporation, Part #R002A); Sau 3AI, Endonuclease Sau 3AI, (Promega Corporation, 8 U/μl, Part #R619E); Bam H1, Endonuclease Bam H1 (Promega Corporation, 10 U/μl, Part #R602A). The solutions were incubated at 37° C. for 1 hr, then heated at 70° C. for 10 min, and allowed to cool to room temperature. The solutions were then added to the reactions presented in Table 46. The reactions were incubated at 37° C. for 20 min. After incubation, 2 μl of the reaction solution was added to 100 μl of L/L reagent and the light output of the reactions was immediately measured using a Turner TD-20e luminometer. The data is presented in Table 46.

These data again demonstrate that detection of DNA by pyrophosphorylation is possible. In addition, these data demonstrate that digestion of plasmid DNA is needed prior to treatment using reverse transcriptase. Bam H1 produces only one DNA fragment from the plasmid while Sau 3A produces over 10 fragments from this plasmid. These data demonstrate that light production increases with increasing fragment end number.

TABLE 45

| Solution | Plasmid | Buffer | Water | Sau 3A | Bam H1 |
|---|---|---|---|---|---|
| 1 | 1 μl | 5 μl | 44 μl | — | — |
| 2 | — | 5 μl | 45 μl | — | — |
| 3 | — | 5 μl | 44 μl | — | 1 μl |
| 4 | — | 5 μl | 44 μl | 1 μl | — |
| 5 | 1 μl | 5 μl | 43 μl | — | 1 μl |
| 6 | 1 μl | 5 μl | 43 μl | 1 μl | — |

TABLE 46

| Reaction | MM | MMLV-RT | Solution | Light |
|---|---|---|---|---|
| Rx1− | 18 μl | — | 1 μl #1 | 0.87 |
| Rx1+ | 18 μl | 1 μl | 1 μl #1 | 0.787 |
| Rx2− | 18 μl | — | 1 μl #2 | 0.906 |
| Rx2+ | 18 μl | 1 μl | 1 μl #2 | 0.75 |
| Rx3− | 18 μl | — | 1 μl #3 | 0.932 |
| Rx3+ | 18 μl | 1 μl | 1 μl #3 | 0.714 |
| Rx4− | 18 μl | — | 1 μl #4 | 0.856 |
| Rx4+ | 18 μl | 1 μl | 1 μl #4 | 0.713 |
| RX5− | 18 μl | — | 1 μl #5 | 0.837 |
| Rx5+ | 18 μl | 1 μl | 1 μl #5 | 2.909 |
| Rx6− | 18 μl | — | 1 μl #6 | 0.811 |
| Rx6+ | 18 μl | 1 μl | 1 μl #6 | 8.757 |

Example 29
Demonstration of DNA Detection Using Pyrophosphorylation Catalyzed by a Thermostable DNA Polymerase Both reverse transcriptases and DNA polymerases catalyze the addition of nucleotides to a DNA strand. As shown in the earlier examples, reverse transcriptases can be used to catalyze the pyrophosphorylation of DNA thereby allowing its detection using coupled enzymatic reactions. In this example, we demonstrate that DNA polymerases also can be used to catalyze this reaction and that the DNA polymerase from Thermus aquaticus (Taq) in fact produces more light from a set amount of input DNA than does the reverse transcriptase.

A master mix (MM) was made which comprised: 10×buffer (Promega Part #M190G, Lot #7675526), 20 μl, 25 mM MgCl$_2$, 40 μl, 40 mM Sodium Pyrophosphate, 5 μl Taq DNA Polymerase (Promega Part #M166B, Lot #7474623) [storage buffer b], 5 U/μl, 10 μl; water, 100 μl. This solution was mixed by vortex and then used to compose the following reactions: Reactions 1–3 (17.5 μl of master mix, 2.5 μl of 1×TE); Reactions 4–6 (17.5 μl of master mix, 1 μl of 100 pg DNA/μl [PhiX 174 HinF1 Fragments, Promega G175A diluted to the concentration listed using 1×TE buffer], 1.5 μl of 1×TE); and Reactions 7–9 (17.5 μl of master mix, 2.5 μl of 100 pg DNA/μl). The solutions were mixed and 30 μl of mineral oil was used to cover the aqueous solution. The solutions were incubated at 70° C. for 30 min. Fifteen microliters were removed to which 1 μl of 1 U/μl NDPK and 1.5 μl of 1 uM ADP were added. After an additional 15 min at room temperature, 2.3 μl of each sample was added to 100 μl of L/L reagent. The light output of the reactions were immediately measured using a luminometer. The data is presented in Table 47.

These results demonstrate the pyrophosphorylation reaction can be catalyzed by DNA polymerases and that low amounts of DNA may be detected. The values obtained from reactions with 10 and 25 pg of DNA are statistically different from the no DNA addition values.

TABLE 47

| Reactions | DNA* | Light Units Measured | | | Mean | Sd. | p-value** |
|---|---|---|---|---|---|---|---|
| 1–3 | 0 pg | 0.915 | 0.653 | 0.837 | 0.802 | 0.135 | |
| 4–6 | 10 pg | 5.718 | 7.718 | 7.397 | 6.958 | 1.089 | <.0094 |
| 7–9 | 25 pg | 11.8 | 11.18 | 14.79 | 12.59 | 1.93 | <.0086 |

*amount of DNA present in the luciferase assay tube
**p value for comparison of the results from no DNA addition to this Mentioned in earlier examples, any value < 0.05 is usually considered a significant difference Example 30
Additional DNA Detection Experiments This example is a direct comparison of the detection of DNA by a reverse transcriptase (MMLV-RT) a thermostable DNA polymerase (Taq Polymerase) and a non-thermostable DNA Polymerase (T4 DNA Polymerase). Also shown is another example of how the particular structure of the DNA fragments utilized in the reaction must be matched to the properties of the DNA modifying enzyme. The enzymes generally fail to produce a signal from supercoiled plasmid DNA since all these enzymes require a DNA end to start their reactions. MMLV-RT RT and Taq DNA Polymerase utilize DNA species having a 5' overhang but cannot use a DNA having a 3' overhang as a substrate. In contrast, T4 DNA Polymerase utilizes DNA substrates with both 5' overhangs and 3' overhangs. This ability may be due to its 3' exonuclease activity. In addition, this Example shows that reactions using T4 DNA polymerase produce more light than from equivalent reactions with either of the other two enzymes.

The reactions were assembled as presented in Table 48. The solutions were incubated at 37° C. for 1 hr then at 70° C. for 10 min. At this point, 1 μl of each reaction was diluted to 20 μl with water to give a concentration of 1000 pg DNA/μl. Solution MM was made as follows: 40 μl 5×MMLV-RT Reaction Buffer (Promega Part M531A); 5 μl 40 mM Sodium pyrophosphate; 20 μl 1 μM ADP; 5 μl 1 U/μl NDPK; and 180 μl water. The reactions were mixed and 18 μl were transferred into 8 tubes. One microliter of reaction 1 above and 1 μl of MMLV-RT (200 U/μl) were added to tubes 1 and 2; 1 μl of reaction 2 above and 1 μl of MMLV-RT were added to tubes 3 and 4; 1 μl of reaction 3 above and 1 μl of MMLV-RT were added to tubes 5 and 6; and 1 μl of reaction 3 was added to tubes 7 and 8. The tubes were incubated 20 min at 37° C. and then 2 μl of the solutions were added to 100 μl of L/L and the light output of the resulting mixture was immediately measured using a Turner TD-20e luminometer. The data is presented in Table 49.

A second MM Mix was made for use with T4 DNA Polymerase as follows: 20 μl 10×Buffer C (Promega Part #R003A); 5 μl 40 mM sodium pyrophosphate; 20 μl 1 μM ADP; 5 μl 1 U/μl NDPK; and 130 μl water. This solution was mixed by vortex and then used to compose the 8 reaction mixtures described in the paragraph above. Incubations were performed at 37° C. for 20 min and then 2 μl of the reaction mixtures were added to 100 μl of L/L with luciferase. The light output was immediately measured and the data presented in Table 50 was obtained.

These data show that both of these enzymes can pyrophosphorylate DNA having 5' overhangs. However the T4 DNA polymerase can also pyrophosphorylate DNA having 3' overhangs (produced by Sph I digestion of DNA) while the reverse transcriptase cannot utilize this form of DNA.

A final MM Mix was made containing: 20 μl 10×Taq Buffer (Promega Part #M190 G); 40 μl 25 mM MgCl$_2$; 5 μl 40 mM sodium pyrophosphate, and 105 μl of water. This new MM Mix was used to produce 8 mixtures. Mixture 1 and 2 contained 17 μl of this new MM Mix, 1 μl of diluted DNA reaction 1, and 2 μl of Taq DNA Polymerase (Promega Part #M166B); mixtures 3 and 4 contained 17 μl MM, 1 μl from reaction 2, and 2 μl Taq; mixtures 5 and 6 contained 17 μl MM, 1 μl from reaction 3, and 2 μl Taq; and mixture 7 and 8 contained 17 μl MM and 1 μl from reaction 3. The mixtures were mixed by vortex action, 30 μl of mineral oil was placed over the tubes and they were incubated at 70° C. for 20 min. Fifteen microliters of each tube was removed and 1 μl of 1 U/μl of NDPK and 1.5 μl of 1 μM ADP was added to each tube. The tubes were incubated at room temperature for 15 min, 2.3 µl were removed from each reaction and added to 100 µl of L/L reagent containing luciferase and the light output of the reactions measured immediately using a luminometer. The data is presented in Table 51.

These data show that Taq DNA Polymerase can utilize DNA having a 5' overhang. However, very little light output results when the DNA has a 3' overhang. Thus, Taq polymerase appears to be similar to MMLV-RT in that it will catalyze the pyrophosphorylation of a DNA if it has a 5' overhang but not if it has a 3' overhang. T4 DNA Polymerase will catalyze pyrophosphorylation with either form of DNA overhang. In addition, by comparing all the data it is clear that much more light is produced if the reactions are performed using T4 polymerase than using either of the other enzymes.

TABLE 48

| Reaction | Buffer | DNA | Bam HI | Sph I | Water |
|---|---|---|---|---|---|
| 1 | 5 µl | 1 µl | — | — | 44 µl |
| 2 | 5 µl | 1 µl | 2 µl | — | 42 µl |
| 3 | 5 µl | 1 µl | — | 2 µl | 42 µl |

The solutions used were:
Buffer, Promega Buffer B (Part #R002A);
DNA, pGEM 3ZF+ (1 mg/ml), Promega Part #P227A;
Bam HI, Promega Bam HI, Part #R602A,
Sph I, Promega Sph I, Part#R626A

TABLE 49

| Reaction | Light Units | DNA Condition | MMLV-RT Added |
|---|---|---|---|
| 1 | 1.472 | supercoiled | + |
| 2 | 1.445 | supercoiled | + |
| 3 | 5.156 | linear, 5' overhang | + |
| 4 | 4.699 | linear, 5' overhang | + |
| 5 | 1.504 | linear, 3' overhang | + |
| 6 | 1.494 | linear, 3' overhang | + |
| 7 | 1.412 | linear, 3' overhang | − |
| 8 | 1.378 | linear, 3' overhang | − |

TABLE 50

| Reaction | Light Units | DNA condition | T4 DNAP added |
|---|---|---|---|
| 1 | 2.214 | supercoiled | + |
| 2 | 1.946 | supercoiled | + |
| 3 | 44.46 | linear, 5' overhang | + |
| 4 | 32.53 | linear, 5' overhang | + |
| 5 | 37.29 | linear, 3' overhang | + |
| 6 | 32.11 | linear, 3' overhang | + |
| 7 | 1.446 | linear, 3' overhang | − |
| 8 | 1.361 | linear, 3' overhang | − |

TABLE 51

| Reaction | Light Units | DNA Condition | Taq DNAP added |
|---|---|---|---|
| 1 | 1.125 | supercoiled | + |
| 2 | 1.174 | supercoiled | + |
| 3 | 8.110 | linear, 5' overhang | + |
| 4 | 9.687 | linear, 5' overhang | + |
| 5 | 1.623 | linear, 3' overhang | + |
| 6 | 1.515 | linear, 3' overhang | + |
| 7 | 1.004 | linear, 3' overhang | − |
| 8 | 1.046 | linear, 3' overhang | − |

Example 31

Detection of Genomic DNA

In this example, high molecular weight DNA is measured using pyrophosphorylation of the DNA, transfer of the terminal phosphate from the dNTPs to ADP to form ATP and measurement of the ATP using Luciferase. High molecular weight DNA can be detected at a higher sensitivity if it is first cleaved using endonucleases.

The reactions were assembled as in Table 52. The materials used in the reactions were: Buffer; 10×Multicore Buffer (Promega Part #R999A); Yeast DNA, S. cerevisiae DNA (380 µg/ml) (Promega Part #G301A); Mouse DNA (300 µg/ml) (Promega Part #G309A); Eco RI, Endonuclease Eco RI, 12 u/µl (Promega Part #R601A). The reactions were heated at 37° C. for 60 min then at 70° C. for 10 min. At that point, 1 µl of each of these reactions were diluted to 20 µl by the addition of 19 µl of water.

A solution (MM) was made which contained: 24 µl of 10×Buffer C (Promega Part #R003A); 6 µl of 40 mM Sodium Pyrophosphate, 24 µl of 1 µM ADP, 6 µl of 1 u/µl NDPK, and 156 µl of water. The reactions presented in Table 53 were assembled using this mix.

The added DNAs in the reactions 1A through 10A above refer to the diluted materials from reactions 1–4 described in Table 53. The T4 DNA Pol is T4 DNA Polymerase (Promega Part #M421F). These reactions were incubated at 37° C. for 20 min, then 2 µl of the reactions was added to 100 µl of L/L reagent. The light produced by the reactions was immediately measured using a Turner TD-20e luminometer. The data is presented in Table 54. Note that the reactions demonstrate that the system can detect genomic DNA. In addition, Eco RI treatment prior to pyrophosphorylation results in higher light values than are seen without Eco RI pretreatment.

TABLE 52

| Reaction | Buffer | Yeast DNA | Mouse DNA | Water | Eco RI |
|---|---|---|---|---|---|
| 1 | 5 µl | 2.6 µl | — | 42.4 µl | — |
| 2 | 5 µl | — | 3.3 µl | 41.7 µl | — |
| 3 | 5 µl | 2.6 µl | — | 40.4 µl | 2 µl |
| 4 | 5 µl | — | 3.3 µl | 39.7 µl | 2 µl |

TABLE 53

| Reaction | MM | DNA Added | T4 DNA Pol |
|---|---|---|---|
| 1A and 2A | 18 µl | 1 µl #1 | 1 µl |
| 3A and 4A | 18 µl | 1 µl #2 | 1 µl |
| 5A and 6A | 18 µl | 1 µl #3 | 1 µl |
| 7A and 8A | 18 µl | 1 µl #4 | 1 µl |
| 9A | 18 µl | 1 µl #3 | — |
| 10A | 18 µl | 1 µl #4 | — |

TABLE 54

| Reaction Sampled | Light Units | Eco R1 Treatment | T4 DNA Pol Treatment |
|---|---|---|---|
| 1A | 2.424 | − | + |
| 2A | 1.94 | − | + |
| 3A | 1.989 | − | + |
| 4A | 1.665 | − | + |
| 5A | 12.27 | + | + |
| 6A | 11.9 | + | + |
| 7A | 23.23 | + | + |

TABLE 54-continued

| Reaction Sampled | Light Units | Eco R1 Treatment | T4 DNA Pol Treatment |
|---|---|---|---|
| 8A | 20.26 | + | + |
| 9A | 0.651 | + | − |
| 10A | 0.724 | + | − |

Example 32
Optimization of ADP Concentrations Used in DNA Detection by Pyrophosphorylation In this example, we examine the effect of varying the ADP concentration on the detection of DNA by the T4 DNA Polymerase catalyzed pyrophosphorylation of the DNA and transfer of the terminal phosphates of the dNTPs to ADP using NDPK. Increasing the concentration of ADP increases the background seen without ATP addition. Increasing the ADP concentration also can increase the signal seen upon DNA pyrophosphorylation. An optimal amount of added ADP can be determined by selecting the concentration of ADP which results in the best fold increase in signal over background.

ADP (Sigma potassium ADP, A-5285, Lot #56H7815) was dissolved in distilled water to various concentrations ranging from 0.2 to 20 µM. The Bam HI digest of pGEM 3ZF+ described in example 26 above was used to form a reaction solution (solution MM) composed of: 40 µl 10×Buffer C (Promega Part #R003A), 10 µl of 40 mM sodium pyrophosphate; 10 µl of 1 u/µl of NDPK; 1 µl of 20 ng/µl Bam HI digested pGEM 3ZF+; and 299 µl of water. These solutions were used to compose the reactions presented in Table 55.

As ADP concentration increases, the total light value increases for both the reactions containing polymerase and those without polymerase as demonstrated in Table 56. In this example the best fold increase in the signal, as defined as fold increase in signal over background, is seen with 0.05 µM ADP in the pyrophosphorylation reaction.

TABLE 55

| Reaction | RM | T4 DNA Pol | ADP |
|---|---|---|---|
| 1, 2 | 18 µl | 1 µl | 1 µl of 0.2 uM |
| 3 | 18 µl | — | 1 µl of 0.2 µM |
| 4, 5 | 18 µl | 1 µl | 1 µl of 1 µM |
| 6 | 18 µl | — | 1 µl of 1 µM |
| 7, 8 | 18 µl | 1 µl | 1 µl of 2 µM |
| 9 | 18 µl | — | 1 µl of 2 µM |
| 10, 11 | 18 µl | 1 µl | 1 µl of 10 µM |
| 12 | 18 µl | — | 1 µl of 10 µM |
| 13, 14 | 18 µl | 1 µl | 1 µl of 20 µM |
| 15 | 18 µl | — | 1 µl of 20 µM |

The T4 DNA Pol used was Promega T4 DNA Polymerase (10 u/ul) (Pt# M421F).

TABLe 56

| Reaction | Light | ADP | DN | Avg. | Blank Avg. | Fold Above no polymerase |
|---|---|---|---|---|---|---|
| 1 | 9.19 | 0.01 µM | + | 8.81 | 8.317 | 16.9 |
| 2 | 8.43 | 0.01 µM | + | | | |
| 3 | 0.43 | 0.01 µM | − | | | |
| 4 | 28.36 | 0.01 µM | + | 29.05 | 28.39 | 42.9 |
| 5 | 29.74 | 0.05 µM | + | | | |
| 6 | 0.662 | 0.05 µM | − | | | |
| 7 | 43.29 | 0.10 µM | + | 41.54 | 40.18 | 29.6 |
| 8 | 39.78 | 0.10 µM | + | | | |
| 9 | 1.359 | 0.10 µM | − | | | |
| 10 | 77.4 | 0.50 µM | + | 74.9 | 68.9 | 11.5 |
| 11 | 72.49 | 0.50 µM | + | | | |
| 12 | 5.969 | 0.50 µM | − | | | |
| 13 | 82.4 | 1.0 µM | + | 80.1 | 69.38 | 6.42 |
| 14 | 77.98 | 1.0 µM | + | | | |
| 15 | 10.81 | 1.0 µM | − | | | |

Example 33
Detection of ATP Using Fluorescence-based Methods

In addition to detecting ATP by luciferase-based methods, ATP can be detected using fluorescence-based systems. For the fluorescence-based measurements, an ATP determination kit was used (Sigma #366-A Lot#117H6017). This kit uses a combination of 2 enzymes, phosphoglycerate kinase and glyceraldehyde phosphate dehydrogenase, to catalyze the formation of NAD from NADH in the presence of ATP. Since the NADH is fluorescent, but the NAD is not, ATP can be measured as a loss in fluorescence intensity. The reaction buffer was prepared from kit components as follows: 3 ml of the supplied buffer solution was diluted in 5.25 ml of nanopure water, and 0.75 ml of 12% trichloroacetic acid was added. One vial of the supplied NADH was reconstituted in 1 ml of nanopure water; the enzyme mix was used as supplied. For each measurement, 10 µl of enzyme mix and 20 µl of NADH were added to 1.5 ml of reaction buffer in a clear plastic 10 mm cuvette. Fluorescence was read in a SPEX Fluorolog Fluorimeter using SPEX dm3000 Software, with absorbance and emission wavelengths set at 340 nm and 460 nm, respectively.

ATP samples at various concentrations were prepared by serially diluting ATP tenfold into 10 mM Tris, pH 7.3. Varying amounts of each dilution was added to the cuvette and the decrease in fluorescence was recorded (Table 57). For comparison ATP was also quantitated using luciferase. 20 µl of each ATP dilution was added to 100 µl LAR with 10 ng of luciferase and light output was measured using a TD-20e luminometer. Each dilution was measured in duplicate (Table 58).

This example indicates that ATP can be detected by at least two separate methods. In the fluorescence-based system, changes of approximately 200,000 fluorescent light units were significant, which corresponds to 1 nanomole of ATP. The luciferase assay was sensitive to lower levels of ATP.

TABLE 57

| ATP Concentration | Volume Added | Mass Added | Decrease in Fluorescence Units in 10,000's | | |
|---|---|---|---|---|---|
| 10 mM | 20 µl | 200 nmoles | 135 | nd[a] | nd[a] |
| 1 mM | 20 µl | 20 nmoles | 84.3 | 132 | nd[a] |
| 1 mM | 10 µl | 10 nmoles | 89.3 | nd[a] | nd[a] |
| 1 mM | 5 µl | 5 nmoles | 76.4 | nd[a] | nd[a] |
| 100 µM | 40 µl | 4 nmoles | 66.7 | 60.2 | nd[a] |
| 100 µM | 20 µl | 2 nmoles | 23.9 | 21.9 | 20.8 |
| 100 µM | 10 µl | 1 nmole | 19.1 | 22.0 | 18.9 |
| 100 µM | 5 µl | 500 pmoles | 7.6 | 6.9 | 6.8 |
| 10 µM | 20 µl | 200 pmoles | 11.6 | 10.0 | 11.1 |
| 10 µM | 10 µl | 100 pmoles | 10.4 | 6.9 | 6.6 |
| 1 µM | 20 µl | 20 pmoles | 8.2 | 8.4 | 5.2 |

TABLE 57-continued

| ATP Concentration | Volume Added | Mass Added | Decrease in Fluorescence Units in 10,000's | | |
|---|---|---|---|---|---|
| 1 μM | 10 μl | 10 pmoles | 8.0 | 8.1 | 5.3 |
| 0.1 μM | 20 μl | 2 pmoles | 3.2 | 5.6 | 3.6 |
| 0.01 μM | 20 μl | 200 fmoles | 8.1 | 9.7 | 6.8 |
| Tris | 20 μl | — | 4.3 | 3.7 | 3.8 |
| Tris | 10 μl | — | 4.0 | 3.3 | 3.5 | nd[a], not done

TABLE 58

| APT, 20 μl of | Light Units | |
|---|---|---|
| 10 mM | 102,417 | 102,731 |
| 1 mM | 117,718 | 98,842 |
| 100 μM | 47,676 | 44,101 |
| 10 μM | 7690 | 6998 |
| 1 μM | 812 | 798 |
| 0.1 μM | 76.8 | 67.8 |
| 0.01 μM | 7.0 | 4.5 |
| Tris | 0.06 | 0.06 |

Example 34

Detection of ATP Using Fluorescence; PRPP Synthetase, Reactions with Adenosine

ATP was synthesized by the enzyme PRPP Synthetase from the substrates AMP and PRPP as in Example 13, except the reactions were done in larger volumes and the substrates were at higher concentrations. 20 μl of AMP (29 mM) and 20 μl of PRPP (26 mM) were incubated with 20 μl of PRPP Synthetase ($6 \times 10^{-3}$ units) in 200 μl of PRPP Synthetase buffer. The reactions are summarized in Table 59. After a 30 minute incubation at 37° C., the PRPP Synthetase was heat-inactivated at 94° C. for 10 minutes. The ATP was then quantitated using both a fluorescence-based system and a luciferase-based system. For the fluorescence-based measurements, an ATP determination kit was used (Sigma #366-A Lot#117H6017) as described in Example 33. Twenty microliter aliquots of the PRPP reactions were then added to cuvettes containing 1.5 ml of buffer, 10 μl of enzyme mix and 20 μl of NADH. The decrease in fluorescence was monitored. Four to six measurements were made for each reaction (Table 60). For the luciferase-based assay, 20 μl was added to 100 μl of LAR and 10 ng of luciferase. Each reaction was determined in triplicate. Light output was measured using a Turner TD-20e luminometer (Table 61). This example demonstrates that ATP production by PRPP Synthetase can be measured using fluorescence or luciferase.

TABLE 59

| Reaction | PRPP Syn Buffer | AMP | PRPP | PRPP Synthetase |
|---|---|---|---|---|
| 1 | 200 μl | 20 μl | 20 μl | 20 μl |
| 2 | 200 μl | 20 μl | — | 20 μl |
| 3 | 200 μl | — | 20 μl | 20 μl |
| 4 | 200 μl | 20 μl | 20 μl | — |

TABLE 60

| Reaction | Decrease in Fluorescence Units (in 10,000's) | | | | | | Average |
|---|---|---|---|---|---|---|---|
| 1 | 49.1 | 48.0 | 47.3 | 49.0 | nd[a] | nd[a] | 48.4 |
| 2 | 2.48 | 3.30 | 2.37 | 10.9 | 7.06 | 9.57 | 5.95 |
| 3 | 3.36 | 2.30 | 11.06 | 7.63 | 10.5 | nd[a] | 6.97 |
| 4 | 3.48 | 1.68 | 4.83 | 0.62 | 5.74 | 3.37 | 3.29 | nd[a], not done

TABLE 61

| Reaction | Light Units | | |
|---|---|---|---|
| 1 | 8923 | 9995 | 9562 |
| 2 | 0.001 | 0.000 | 0.013 |
| 3 | 1939 | 1760 | 1770 |
| 4 | 27.9 | 23.7 | 23.0 |

Example 35

Detection of ATP Using Fluorescence; Cell Lysates

ATP can also be generated by incubating cell lysates with AMP and dCTP as described in Examples 25, 26 and 27. The Sigma ATP determination kit described in Example 33 was also used to detect ATP in this system. Reactions were assembled as described below (Table 62) and incubated at room temperature. ATP concentrations were quantitated at 80 minutes and 140 minutes using luciferase. In this assay 15 μl of each reaction was added to 100 μl of LAR and 10 ng of luciferase. Light output was measured using a Turner Luminometer TD-20e (Table 63). During the time course, ATP was also measured by fluorescence. The procedure was as described in Example 33, except that 15 μl of each reaction was added per reading, instead of 20 μl. The first set of time points began at 80 minutes; the second set of readings began at 140 minutes. Each reaction was assayed in duplicate or triplicate (Table 64). This example demonstrates that ATP synthesized in cell lysates can be detected using a luciferase or a fluorescence assay.

TABLE 62

| Reaction | E. coli Lysate | 0.05 M MgSO₄ | 10 mM AMP | 100 mM dCTP |
|---|---|---|---|---|
| 1 | 100 μl | 20 μl | 20 μl | 10.5 μl |
| 2 | — | 20 μl | 20 μl | 10.5 μl |
| 3 | 100 μl | — | 20 μl | 10.5 μl |
| 4 | 100 μl | 20 μl | — | 10.5 μl |
| 5 | 100 μl | — | — | 10.5 μl |

TABLE 63

| Reactions | Light Units T = 80 minutes | T = 140 minutes |
|---|---|---|
| 1 | 33,519 | 65,522 |
| 2 | 2.158 | 2.086 |
| 3 | 362.7 | 370.6 |
| 4 | 0.5 | 0.561 |
| 5 | 1.898 | 1.057 |

TABLE 64

| | Decrease in Fluorescence Units (in 10,000's) | | | |
|---|---|---|---|---|
| Reaction | First Time Point | | Second Time Point | |
| 1 | 27.1 | 29.4 | 83.8 | 87.3 |
| 2 | 11.9 | 8.2 | 1.3 | 1.2 |
| 3 | 12.2 | 8.2 | 4.1 | 4.7 |
| 4 | 5.0 | 4.1 | 4.2 | 2.8 |
| 5 | nd[a] | nd[a] | 4.8 | 7.3 | nd[a], not done

Example 36
Extremely Sensitive DNA Measurement by Amplification of Pyrophosphorylation Reaction Products This Example demonstrates that AMP can be a source of extraneous nucleotides that result in unwanted background amplification in reactions spiked with a nucleoside triphosphate and that the detection limit for DNA measured through the pyrophosphorylation of the sample can be lowered if the products are amplified.

Two reactions were assembled. Reaction 1 consisted of: 2 µl of 10×Buffer C (Promega Corp. R003A, Lot 7544205); 0.5 µl of 40 nM sodium pyrophosphate; 2 µl of 1 mM AMP; 1 ul of 0.25 U/µl Myokinase (Sigma M3003, Lot 116H9516); 1 µl of 0.17 U/ul Pyruvate Kinase (Sigma N 0379, Lot 127F81802); 1 µl of 10 U/µl T4 DNA Polymerase (Promega M421F Lot 617506) and 11.5 µl of water. Reaction 2 was identical to Reaction 1 except that the AMP was treated with Apyrase in a reaction consisting of 20 µl of 10 mM AMP and 1 µl of 1 U/µl Apyrase (Sigma A 6535 lot 127H7010) for 30 min at room temperature, followed by a heat inactivation step to eliminate the Apyrase activity by treatment at 70° C. for 10 Min.

At time 0, 1 µl of 10 mM PEP was added to each reaction and the reaction was mixed and incubated at room temperature. At 2 min, 2 µl of the reaction was removed and added to 100 µl of L/L reagent and the light output measured using a Turner TD-20e Luminometer as described above. The following data were collected: Reaction 1; 817.4 light units, Reaction 2; 7.3 light units. Since there should be no ATP produced by this reaction unless extraneous nucleoside di- or triphosphate is added as a contaminant in a reagent, this demonstrates that the AMP probably contained some level of contaminating nucleotide which was eliminated by Apyrase treatment.

The following reactions were assembled: Reaction A contained the components described in Reaction 2 above except that 1 µl of 1 ng Hin F1 Fragments(Promega Corp, G175A Lot 7733602) diluted to this concentration with 1×TE Buffer )/µl was added and the T4 DNA Polymerase was not added to the initial reaction mix; Reaction B, same as Reaction A but the DNA added was at a concentration of 100 µpg DNA/µl; Reaction C, same as Reaction A but the DNA added was at a concentration of 10 pg DNA/µl; Reaction D, same as Reaction A but the DNA added was at a concentration of 1 pg DNA/µl; and, Reaction E, same as Reaction A but with 1 µl of 1×TE Buffer added and no DNA added.

One microliter of T4 DNA Polymerase was added to each reaction and the reactions were incubated at 37C. for 15 min. After this incubation, 1 µl of 10 mM PEP was added to each reaction and incubated again at room temperature for 10 min. At that time, 2 µl of each reaction was added to 100 µl of L/L reagent and the light output of the reaction was measured using a Turner Luminometer as described above.

The data are presented in Table 65. This Example demonstrates that the products of the pyrophosphorylation reaction can be coupled to an ATP amplification system to increase the sensitivity of DNA measurement.

TABLE 65

| | | Light Measured From Samples Incubated at Room Temperature | |
|---|---|---|---|
| | pg DNA* | 10 min | 20 min |
| A | 100 pg | 917.3 | 1156 |
| B | 10 pg | 112.1 | 1119 |
| C | 1 pg | 4.68 | 919 |
| D | 0.1 pg | 2.61 | 873 |
| E | 0 | 1.52 | 650 |

*The DNA reported in this column is the actual DNA equivalent Luciferase reaction. The amount is approximately 10% of the total pyrophosphorylated.

What is claimed is:

1. A method for determining the presence and/or amount of cells and cellular material, the method comprising:
    releasing the contents of cells to form a cell lysate;
    adding phosphate donor molecules and adenosine 5'-monophosphate molecules to the cell lysate so that adenosine 5'-diphosphate molecules are produced by the enzymatic transfer of a phosphate group from the donor to the adenosine 5'-monophosphate according to the following general reaction catalyzed by endogenous enzymes present in the cell lysate:

D-P+AMP→D+ADP;

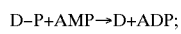

and
    producing adenosine 5'-triphosphate by the enzymatic transfer of a phosphate group from the donor molecules to the adenosine 5'-diphosphate molecules according to the following general reaction catalyzed by endogenous enzymes present in the cell lysate sample:

D-P+ADP→D+ATP;

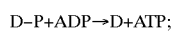

and
    detecting the adenosine 5'-triphosphate produced thereby.

2. The method of claim 1 wherein the phosphate donor is selected from the group consisting of deoxycytidine 5'-triphosphate, deoxyguanidine 5' triphosphate and deoxythymidine 5' triphosphate.

3. A composition of matter for producing adenosine 5'-triphosphate from DNA, pyrophosphate, and adenosine 5'-diphosphate, the composition comprising a mixture of:
    a nucleoside diphosphate kinase; and
    a nucleic acid polymerase, the nucleoside diphosphate kinase and the nucleic acid polymerase provided in a sufficient concentration to catalyze the production of the adenosine triphosphate from DNA at about picogram to microgram amounts of DNA.

4. A composition of matter for producing adenosine triphosphate from DNA, phosphoribosylpyrophosphate and adenosine 5'-diphosphate, the composition comprising a mixture of:
    a phosphoribosylpyrophosphate synthetase; and
    a nucleoside diphosphate kinase, the phosphoribosylpyrophosphate synthetase and nucleoside diphosphate kinase in a sufficient concentration to catalyze the production of the adenosine triphosphate from about picogram to microgram amounts of DNA.

5. A method of producing a plurality of adenosine triphosphate molecules from a nucleoside triphosphate molecule in a reaction containing adenosine 5'-monophosphate molecules, high energy phosphate donor molecules, or a combination thereof, the method comprising the steps of:

(1) enzymatically transferring the terminal 5' phosphate group from a nucleoside triphosphate molecule present in the sample to an adenosine 5'-monophosphate molecule added to the sample to form an adenosine 5'-diphosphate molecule and nucleoside diphosphate molecule according to the following general reaction catalyzed by a first enzyme:

XTP+AMP→XDP+ADP;

(2) enzymatically transferring a phosphate group from a high energy phosphate donor molecule which may not be utilized by the first enzyme to adenosine 5'-diphosphate molecules to form adenosine 5'-triphosphate molecules according to the following general reaction catalyzed by nucleoside diphosphate kinase:

ADP+D-P=ATP+D;

and (3) amplifying the adenosine triphosphate molecule so produced by repeating steps (1) and (2) until the desired level of amplification is achieved.

6. The method of claim 5 wherein the first enzyme is selected from the group consisting of nucleoside monophosphate kinase and adenylate kinase.

7. The method of claim 5 wherein the high energy phosphate donor is selected from the group of dCTP and AMP-CPP.

8. A method of producing a plurality of adenosine triphosphate molecules from a nucleoside triphosphate molecule according to claim 5 wherein said nucleoside triphosphate molecules are formed in a process comprising the steps of:

(a) providing poly(A)-mRNA in a reaction containing pyrophosphate, adenosine 5'-disphosphate, or a combination thereof, (b) hybridizing a complimentary oligo(dT) probe to poly (A)-mRNA to form a RNA-DNA hybrid, (c) depolymerizing the oligo(dT) strand of the RNA-DNA hybrid at the terminal nucleotide enzymatically cleaving the terminal internucleotide phosphodiester bond and reforming same with a pyrophosphate molecule to form a deoxythymidine 5'-triphosphate molecule according to the following general reaction catalyzed by a reverse transcriptase:

$dRR_n * \times PPi \rightarrow dTT_{n-1} \times dTTP$; and (d) repeating the depolymerizing step to obtain at least two nucleoside triphosphate molecules;

said process comprising the further steps of:

(e) enzymatically transferring terminal 5' phosphate groups from the deoxythymidine 5'-diphosphate molecules to form adenosine 5'-triphosphate molecules according to the following general reaction:

$dTTP* \times ADP = dTDP \times ATP*$, wherein P* is the terminal 5' phosphate so transferred; and (f) detecting the adenosine 5'-triphosphate formed thereby.

* * * * *